United States Patent [19]
Robinson

[11] Patent Number: 6,110,964
[45] Date of Patent: Aug. 29, 2000

[54] BICYCLIC HYDROXAMIC ACID DERIVATIVES

[75] Inventor: Ralph Pelton Robinson, Gales Ferry, Conn.

[73] Assignee: Pfizer Inc., New York, N.Y.

[21] Appl. No.: 09/402,259

[22] PCT Filed: Mar. 24, 1999

[86] PCT No.: PCT/IB99/00503

§ 371 Date: Sep. 30, 1999

§ 102(e) Date: Sep. 30, 1999

[87] PCT Pub. No.: WO99/52910

PCT Pub. Date: Oct. 21, 1999

Related U.S. Application Data

[60] Provisional application No. 60/081,309, Apr. 10, 1998.
[51] Int. Cl.⁷ .......................... A61K 31/35; C07D 311/00
[52] U.S. Cl. .............................. 514/456; 549/397
[58] Field of Search .................. 549/397; 514/456

[56] References Cited

U.S. PATENT DOCUMENTS

| | | | |
|---|---|---|---|
| 3,538,117 | 11/1970 | Tobey et al. | 549/397 |
| 4,221,721 | 9/1980 | Sprecker et al. | 549/397 |
| 4,588,821 | 5/1986 | Powell | 549/397 |
| 4,861,913 | 8/1989 | Narisada et al. | 562/427 |
| 5,204,333 | 4/1993 | Larkin et al. | 514/456 |
| 5,863,949 | 1/1999 | Robinson et al. | 514/575 |

*Primary Examiner*—Deborah C. Lambkin
*Attorney, Agent, or Firm*—Peter C. Richardson; Paul H. Ginsburg; Polene W. Appleman

[57] ABSTRACT

A compound of the formula

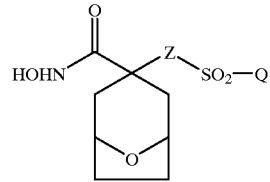

I wherein Z and Q are as defined in the specification, to pharmaceutical compositions containing them and to their medicinal use.

27 Claims, No Drawings

BICYCLIC HYDROXAMIC ACID DERIVATIVES

This application is a 371 of PCT/IB99/00503 Mar. 24, 1999 provisional application No. 60/081,309 Apr. 10, 1998.

The present invention relates to bicyclic hydroxamic acid derivatives, and to pharmaceutical compositions and methods of treatment.

The compounds of the present invention are inhibitors of zinc metalloendopeptidases, especially those belonging to the matrix metalloproteinase (also called MMP or matrixin) and reprolysin (also known as adamylsin) subfamilies of the metzincins (Rawlings, et al., *Methods in Enzymology,* 248, 183–228 (1995) and Stocker et al., *Protein Science,* 4, 823–840 (1995)). The MMP subfamily enzymes, currently contains seventeen members (MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20). The MMP's are most well known for their role in regulating the turn-over of extracellular matrix proteins and as such play important roles in normal physiological processes such as reproduction, development and differentiation. In addition, the MMP's are expressed in many pathological situations in which abnormal connective tissue turnover is occurring. For example, MMP-13 an enzyme with potent activity at degrading type II collagen (the principal collagen in cartilage), has been demonstrated to be overexpressed in osteoarthritic cartilage (Mitchell, et al., *J. Clin. Invest.,* 97, 761 (1996)). Other MMPs (MMP-2, MMP-3, MMP-8, MMP-9, MMP-12) are also overexpressed in osteoarthritic cartilage and inhibition of some or all of these MMP's is expected to slow or block the accelerated loss of cartilage typical of joint diseases such as osteoarthritis or rheumatoid arthritis.

The mammalian reprolysins are known as ADAMs (A Disintegrin And Metalloproteinase) (Wolfberg, et al., *J. Cell Biol.,* 131, 275–278 (1995)) and contain a disintegrin domain in addition to a metalloproteinase-like domain. To date twenty three distinct ADAM's have been identified.

ADAM-17, also known as tumor necrosis factor-alpha converting enzyme (TACE), is the most well known ADAM. ADAM-17 (TACE) is responsible for cleavage of cell bound tumor necrosis factor-alpha (TNF-α, also known is cachectin). TNF-α is recognized to be involved in many infections and auto-immune diseases (W. Friers, *FEBS Letters,* 285, 199 (1991)). Furthermore, it has been shown that TNF-α is the prime mediator of the inflammatory response seen in sepsis and septic shock (Spooner, et al., *Clinical Immunology and Immunopathology,* 62 S11 (1992)). There are two forms of TNF-α, a type II membrane protein of relative molecular mass 26,000 (26 kD) and a soluble 17 kD form generated from the cell bound protein by specific proteolytic cleavage. The soluble 17 kD form of TNF-α is released by the cell and is associated with the deleterious effects of TNF-α. This form of TNF-α is also capable of acting at sites distant from the site of synthesis. Thus, inhibitors of TACE prevent the formation of soluble TNF-α and prevent the deleterious effects of the soluble factor.

Select compounds of the invention are potent inhibitors of aggrecanase, an enzyme important in the degradation of cartilage aggrecan. Aggrecanase is also believed to be an ADAM. The loss of aggrecan from the cartilage matrix is an important factor in the progression of joint diseases such as osteoarthritis and rheumatoid arthritis and inhibition of aggrecanase is expected to slow or block the loss of cartilage in these diseases.

Other ADAMs that have shown expression in pathological situations include ADAM TS-1 (Kuno, et al., *J. Biol. Chem.* 272, 556–562 (1997)), and ADAM's 10, 12 and 15 (Wu, et al., *Biochem. Biophys. Res. Comm.* 235, 437–442, (1997)). As knowledge of the expression, physiological substrates and disease association of the ADAM's increases the full significance of the role of inhibition of this class of enzymes will be appreciated.

Diseases in which inhibition of MMP's and or ADAM's will provide therapeutic benefit include: arthritis (including osteoarthritis and rheumatoid arthritis), inflammatory bowel disease, Crohn's disease, emphysema, acute respiratory distress syndrome, asthma chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis, septic shock and other diseases characterized by metalloproteinase or ADAM expression.

This invention also relates to a method of using the compounds of the invention in the treatment of the above diseases in mammals, especially humans, and to the pharmaceutical compositions useful therefore.

It is recognized that different combinations of MMP's and ADAM's are expressed in different pathological situations. As such inhibitors with specific selectivities for individual ADAM's and/or MMP's may be preferred for individual diseases. For example, rheumatoid arthritis is an inflammatory joint disease characterized by excessive TNF level and the loss of joint matrix constituents. In this case, a compound that inhibits TACE and aggrecanase as well as MMP's such as MMP-13 may be the preferred therapy. In contrast, in a less inflammatory joint disease such as osteoarthritis, compounds that inhibit matrix degrading MMP's such as MMP-13 but not TACE may be preferred.

The present inventors have also discovered that it is possible to design inhibitors with differential metalloprotease activity. Specifically, for example, the inventors have been able to design molecules which selectively inhibit matrix metalloprotease-13 (MPP-13) preferentially over MMP-1.

Matrix metalloproteinase inhibitors are well known in the literature. Specifically, PCT Publication WO 96/33172, published Oct. 24, 1996, refers to cyclic arylsulfonylamino hydroxamic acids that are useful as MMP inhibitors. U.S. Pat. No. 5,672,615, PCT Publication WO 97/20824, PCT Publication WO 98/08825, PCT Publication WO 98/27069, and PCT Publication WO 98/34918, published Aug. 13, 1998, entitled "Arylsulfonyl Hydroxamic Acid Derivatives" all refer to cyclic hydroxamic acids that are useful as MMP inhibitors. PCT Publications WO 96/27583 and WO 98/07697, published Mar. 7, 1996 and Feb. 26, 1998, respectively refer to arylsulfonyl hydroxamic acids. PCT Publication WO 98/03516, published Jan. 29, 1998 refers to phosphinates with MMP activity. PCT Publication 98/34915, published Aug. 13, 1998, entitled "N-Hydroxy-b-Sulfonyl Propionamide Derivatives," refers to propionylhydroxamides as useful MMP inhibitors. PCT Publication WO 98/33768, published Aug. 6, 1998, entitled "Arylsulfonylamino Hydroxamic Acid Derivatives," refers to N-unsubstituted arylsulfonylamino hydroxamic acids. PCT Publication WO 98/30566, published Jul. 16, 1998, entitled "Cyclic Sulfone Derivatives," refers to cyclic sulfone hydroxamic acids as MMP inhibitors. U.S. Provisional Patent Application Ser. No. 60/55208, filed Aug. 8, 1997, refers to biaryl hydroxamic acids as MMP inhibitors. U.S. Provisional Patent Application Ser. No. 60/55207, filed Aug. 8, 1997, entitled "Aryloxyarylsulfonylamino Hydroxamic Acid Derivatives." refers to aryloxyarylsulfonyl hydroxamic acids as MMP inhibitors. U.S. Provisional Patent Application No. 60/62766, filed Oct. 24, 1997, entitled "The Use Of MMP-13 Selective Inhibitors For the Treatment of Osteoarthritis and Other MMP Mediated Disorders," refers to the use of MMP-13 selective inhibitors to treat inflammation and other disorders. U.S. Provisional Patent Application Ser. No. 60/68261, filed Dec. 19, 1997, refers to the use of MMP inhibitors to treat angiogenesis and other disorders. Each of the above referenced publications and applications is hereby incorporated by reference in its entirety.

SUMMARY OF THE INVENTION

The present invention relates to a compound of the formula

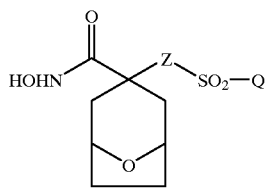

I wherein

Z is <CH$_2$ or <NR$^1$;

R$^1$ is hydrogen, (C$_1$–C$_6$)alkyl, (C$_6$–C$_{10}$)aryl(C$_1$–C$_6$)alkyl, (C$_2$–C$_9$)heteroaryl(C$_1$–C$_6$)alkyl or a group of the formula

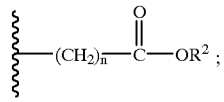

n is an integer from one to six;

R$^2$ is hydrogen or (C$_1$–C$_6$)alkyl;

Q is (C$_1$–C$_6$)alkyl, (C$_6$–C$_{10}$)aryl, (C$_2$–C$_9$)heteroaryl, (C$_6$–C$_{10}$)aryloxy(C$_1$–C$_6$)alkyl, (C$_6$–C$_{10}$)aryloxy (C$_6$–C$_{10}$)aryl, (C$_6$–C$_{10}$)aryloxy(C$_2$–C$_9$)heteroaryl, (C$_6$–C$_{10}$)aryl(C$_1$–C$_6$)alkyl, (C$_6$–C$_{10}$)aryl(C$_6$–C$_{10}$)aryl, (C$_6$–C$_{10}$)aryl(C$_2$–C$_9$)heteroaryl, (C$_6$–C$_{10}$)aryl(C$_6$–C$_{10}$) aryl(C$_1$–C$_6$)alkyl, (C$_6$–C$_{10}$)aryl(C$_6$–C$_{10}$)aryl(C$_6$–C$_{10}$) aryl, (C$_6$–C$_{10}$)aryl(C$_6$–C$_{10}$)aryl(C$_2$–C$_9$)heteroaryl, (C$_2$–C$_9$)heteroaryl(C$_1$–C$_6$)alkyl, (C$_2$–C$_9$)heteroaryl (C$_6$–C$_{10}$)aryl, (C$_2$–C$_9$)heteroaryl(C$_2$–C$_9$)heteroaryl, (C$_6$–C$_{10}$)aryl(C$_1$–C$_6$)alkoxy(C$_1$–C$_6$)alkyl, (C$_6$–C$_{10}$) aryl(C$_1$–C$_6$)alkoxy(C$_6$–C$_{10}$)aryl, (C$_6$–C$_{10}$)aryl(C$_1$–C$_6$) alkoxy(C$_2$–C$_9$)heteroaryl, (C$_2$–C$_9$)heteroaryloxy (C$_1$–C$_6$)alkyl, (C$_2$–C$_9$)heteroaryloxy(C$_6$–C$_{10}$)aryl, (C$_2$–C$_9$)heteroaryloxy(C$_2$–C$_9$)heteroaryl, (C$_2$–C$_9$) heteroaryl(C$_1$–C$_6$)alkoxy(C$_1$–C$_6$)alkyl, (C$_2$–C$_9$) heteroaryl(C$_1$–C$_6$)alkoxy(C$_6$–C$_{10}$)aryl, (C$_2$–C$_9$) heteroaryl(C$_1$–C$_6$)alkoxy(C$_2$–C$_9$)heteroaryl (C$_6$–C$_{10}$) aryloxy(C$_{1-C_6}$)alkyl(C$_6$–C$_{10}$)aryl, (C$_6$–C$_{10}$)aryloxy (C$_1$–C$_6$)alkyl(C$_2$–C$_9$)heteroaryl, C$_2$–C$_9$)heteroaryloxy (C$_1$–C$_6$)alkyl(C$_6$–C$_{10}$)aryl or C$_2$–C$_9$)heteroaryloxy (C$_1$–C$_6$)alkyl(C$_2$–C$_9$)heteroaryl;

wherein each (C$_6$–C$_{10}$)aryl or (C$_2$–C$_9$)heteroaryl moieties of said (C$_6$–C$_{10}$)aryl, (C$_2$–C$_9$)heteroaryl, (C$_6$–C$_{10}$) aryloxy(C$_1$–C$_6$)alkyl, (C$_6$–C$_{10}$)aryloxy(C$_6$–C$_{10}$)aryl, (C$_6$–C$_{10}$)aryloxy(C$_2$–C$_9$)heteroaryl, (C$_6$–C$_{10}$)aryl (C$_1$–C$_6$)alkyl, (C$_6$–C$_{10}$)aryl(C$_6$–C$_{10}$)aryl, (C$_6$–C$_{10}$)aryl (C$_2$–C$_9$)heteroaryl, (C$_6$–C$_{10}$)aryl(C$_6$–C$_{10}$)aryl(C$_1$–C$_6$) alkyl, (C$_6$–C$_{10}$)aryl(C$_6$–C$_{10}$)aryl(C$_6$–C$_{10}$)aryl, (C$_6$–C$_{10}$)aryl(C$_6$–C$_{10}$)aryl(C$_2$–C$_9$)heteroaryl, (C$_2$–C$_9$) heteroaryl(C$_1$–C$_6$)alkyl, (C$_2$–C$_9$)heteroaryl(C$_6$–C$_{10}$) aryl, (C$_2$–C$_9$)heteroaryl(C$_2$–C$_9$)heteroaryl, (C$_6$–C$_{10}$) aryl(C$_1$–C$_6$)alkoxy(C$_1$–C$_6$)alkyl, (C$_6$–C$_{10}$)aryl(C$_1$–C$_6$) alkoxy(C$_6$–C$_{10}$)aryl, (C$_6$–C$_{10}$)aryl(C$_1$–C$_6$)alkoxy (C$_2$–C$_9$)heteroaryl, (C$_2$–C$_9$)heteroaryloxy(C$_1$–C$_6$) alkyl, (C$_2$–C$_9$)heteroaryloxy(C$_6$–C$_{10}$)aryl, (C$_2$–C$_9$) heteroaryloxy(C$_2$–C$_9$)heteroaryl, (C$_2$–C$_9$)heteroaryl (C$_1$–C$_6$)alkoxy(C$_1$–C$_6$)alkyl, (C$_2$–C$_9$)heteroaryl (C$_1$–C$_6$)alkoxy(C$_6$–C$_{10}$)aryl, (C$_2$–C$_9$)heteroaryl (C$_1$–C$_6$)alkoxy(C$_2$–C$_9$)heteroaryl, (C$_6$–C$_{10}$)aryloxy (C$_1$–C$_6$)alkyl(C$_6$–C$_{10}$)aryl, (C$_6$–C$_{10}$)aryloxy(C$_1$–C$_6$) alkyl(C$_2$–C$_9$)heteroaryl, (C$_2$–C$_9$)heteroaryloxy(C$_1$–C$_9$) heteroaryloxy(C$_1$–C$_6$)alkyl (C$_6$–C$_{10}$)aryl or (C$_2$–C$_9$) heteroaryloxy(C$_1$–C$_6$)alkyl(C$_2$–C$_9$)heteroaryl is optionally substituted on any of the ring carbon atoms capable of forming an additional bond by one or more substituents per ring independently selected from fluoro, chloro, bromo, (C$_1$–C$_6$)alkyl, (C$_1$–C$_6$)alkoxy, perfluoro(C$_1$–C$_3$)alkyl, perfluoro(C$_1$–C$_3$)alkoxy and (C$_6$–C$_{10}$)aryloxy;

or pharmaceutically accepted salts thereof.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), trimethyl-ammonium or diethylammonium, and the lower alkanolammonium salts such tris-(hydroxymethyl)-methylammonium and other base salts of pharmaceutically acceptable organic amines.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined above.

The term "aryl", as used herein, unless otherwise indicated, includes an organic radical derived from an aromatic hydrocarbon by removal of one hydrogen, such as phenyl or naphthyl.

The term "heteroaryl", as used herein, unless otherwise indicated, includes an organic radical derived from an aromatic heterocyclic compound by removal of one hydrogen, such as pyridyl, furyl, pyroyl, thienyl, isothiazolyl, imidazolyl, benzimidazolyl, tetrazolyl, pyrazinyl, pyrimidyl, quinotyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl. Preferred heteroaryls include pyridyl, furyl, thienyl, osothiazolyl, pyrazinyl, pyrimidyl, pyrazolyl, isoxazolyl, thiazolyl or oxazolyl. Most preferred heteroaryls include pyridyl, furyl and thienyl.

The term "acyl", as used herein, unless otherwise indicated, includes a radical of the general formula R—(C=O)— wherein R is alkyl, alkoxy, aryl, arylalkyl or arylalkoxy and the terms "alkyl" or "aryl" are as defined above.

The term "acyloxy", as used herein, includes O-acyl groups wherein "acyl" is defined above.

The compound of formula I may have chiral centers and therefore exist in different diasteriomeric or enantiomeric forms. This invention relates to all optical isomers, tautomers and stereoisomers of the compounds of formula I and mixtures thereof.

Preferably, compounds of the formula I exist as the exo isomer of the formula

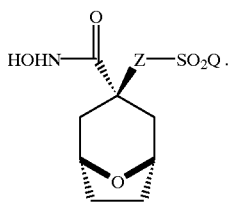

I'

Other preferred compounds of formula I are those wherein Q is $(C_6-C_{10})$aryl, $(C_2-C_9)$heteroaryloxy$(C_6-C_{10})$aryl or $(C_6-C_{10})$aryloxy$(C_6-C_{10})$aryl, wherein each aryl or heteroaryl moiety of said $(C_6-C_{10})$aryl, $(C_2-C_9)$heteroaryloxy$(C_6-C_{10})$aryl or $(C_6-C_{10})$aryloxy$(C_6-C_{10})$aryl groups may be optionally substituted with one or more substituents independently selected from fluoro, chloro, bromo, $(C_1-C_6)$alkyl, $(C_1-C_6)$alkoxy or perfluoro$(C_1-C_3)$alkyl.

More preferred compounds of formula I include those wherein Q is phenyl, pyridyloxyphenyl (more preferably 4-pyridyl) or phenoxyphenyl optionally substituted with one or more substituents independently selected from fluoro, chloro, bromo, $(C_1-C_6)$alkyl, $(C_1-C_6)$alkoxy or perfluoro $(C_1-C_3)$alkyl, more preferably the substituents are selected from fluoro, chloro, $(C_1-C_6)$alkoxy or $(C_1-C_6)$alkyl, most preferably the substituent is in the 4-position.

Specific preferred compounds of formula I include the following:

3-exo-[4-(4-fluorophenoxy)benzenesulfonylamino]-8-oxabicyclo[3.2.1]-octane-3-carboxylic acid hydroxyamide;

3-exo-[4-(4-fluorophenoxy)benzenesulfonylmethyl]-8-oxabicyclo-[3.2.1]-octane-3-carboxylic acid hydroxyamide;

3-(4-phenoxybenzenesulfonylmethyl)-8-oxabicyclo [3.2.1]-octane-3-carboxylic acid hydroxyamide;

3-exo-(4-fluorobiphenyl-4-benzenesulfonylmethyl)-8-oxabicyclo-[3.2.1]-octane-3-carboxylic acid hydroxyamide; and 3-exo-[4-(4-Chlorophenoxy)benzenesulfonylmethyl]-8-oxabicyclo[3.2.1]octane-3-carboxylic acid hydroxyamide.

Other compounds of the invention of formula I include the following:

3-exo-(4-Phenoxybenzenesulfonylamino)-8-oxabicyclo [3.2.1]octane-3-carboxylic acid hydroxyamide, 3-exo-[4-(Pyridin-4-yloxy)benzenesulfonylamino]-8-oxabicyclo[3.2.1]octane-3-carboxylic acid hydroxyamide, 3-exo-[4-(4-Chlorophenoxy)benzenesulfonylamino]-8-oxabicyclo[3.2.1]octane-3-carboxylic acid hydroxyamide, 3-[[4-(4-Chlorophenoxy)benzenesulfonyl]-(3-endo-hydroxycarbamoyl-8-oxabicyclo[3.2.1]oct-3-yl)amino] propionic acid, 3-[[4-(4-Chlorophenoxy)benzenesulfonyl]-(3-endo-hydroxycarbamoyl-8-oxabicyclo[3.2.1]oct-3-yl)amino] propionic acid ethyl ester, 3-[[4-(4-Fluorophenoxy)benzenesulfonyl]-(3-endo-hydroxycarbamoyl-8-oxabicyclo[3.2.1]oct-3-yl)-amino] propionic acid, 3-[[4-(4-Fluorophenoxy)benzenesulfonyl]-(3-endo-hydroxycarbamoyl-8-oxabicyclo[3.2.1]oct-3-yl)-amino] propionic acid ethyl ester, 3-exo{[4-(4-Fluorophenoxy)benzenesulfonyl] methylamino}-8-oxabicyclo[3.2.1]octane-3-carboxylic acid hydroxyamide, 3-endo-[4-(4-Fluorophenoxy)benzenesulfonyl]-8-oxabicyclo[3.2.1]octane-3-carboxylic acid hydroxyamide, 3-exo-{[4-(4-Fluorophenoxy)benzenesulfonyl]pyridin-3-ylmethylamino}-8-oxabicyclo[3.2.1]octane-3-carboxylic acid hydroxyamide, 3-exo-[4-(4-Fluorobenzyloxy)benzenesulfonylamino]-8-oxabicyclo[3.2.1]octane-3-carboxylic acid hydroxyamide, 3-exo-(4-Benzyloxybenzenesulfonylamino)-8-oxabicyclo[3.2.1]octane-3-carboxylic acid hydroxyamide, 3-exo-(4-Benzyloxybenzenesulfonylmethyl)-8-oxabicyclo[3.2.1]octane-3-carboxylic acid hydroxyamide, 3-exo-{Methyl-[4-(pyridin-4-yloxy)benzenesulfonyl] amino}-8-oxabicyclo[3.2.1]octane-3-carboxylic acid hydroxyamide, 3-exo-(4-Methoxybenzenesulfonylamino)-8-oxabicyclo [3.2.1]octane-3-carboxylic acid hydroxyamide, 3-exo-(4-Methoxybenzenesulfonylmethyl)-8-oxabicyclo [3.2.1]octane-3-carboxylic acid hydroxyamide, 3-exo-5-Pyridin-2-ylthiophene-2-sulfonylamino)-8-oxabicyclo[3.2.1]octane-3-carboxylic acid hydroxyamide, 3-exo-(4-Phenoxybenzenesulfonylamino)-8-oxabicyclo [3.2.1]octane-3-carboxylic acid hydroxyamide, 3-exo-[4-(Pyridin-4-yloxy)benzenesulfonylmethyl]-8-oxabicyclo[3.2.1]octane-3-carboxylic acid hydroxyamide, 3-exo-[4-(Pyridin-4-yloxy)benzenesulfonylamino]-8-oxabicyclo[3.2.1]octane-3-carboxylic acid hydroxyamide, 3-exo-[4-(4-Chlorophenoxy)benzenesulfonylmethyl]-8-oxabicyclo[3.2.1]octane-3-carboxylic acid hydroxyamide, 3-exo-[4-(4-Chlorophenoxy)benzenesulfonylamino]-8-oxabicyclo[3.2.1]octane -3-carboxylic acid hydroxyamide, 3-[[4-(4-Fluorophenoxy)benzenesulfonyl]-(3-endo-hydroxycarbamoyl-8-oxabicyclo[3.2.1]oct-3-yl)amino] propionic acid, 3-[(3-endo-Hydroxycarbamoyl-8-oxabicyclo[3.2.1]oct-3-yl)-(4-phenoxybenzenesulfonyl)-amino]propionic acid, 3-exo-{[4-(4-Fluorophenoxy)benzenesulfonyl]pyridin-3-ylmethylamino}-8-oxabicyclo-[3.2.1]octane-3-carboxylic acid hydroxyamide, 3-exo-[(4-Phenoxybenzenesulfonyl)pyridin-3-ylmethylamino]-8-oxabicyclo[3.2.1]octane-3-carboxylic acid hydroxyamide, 3-exo-{Methyl[4-(pyridin-4-yloxy)benzenesulfonyl]
amino}-8-oxabicyclo[3.2.1]octane-3-carboxylic acid
hydroxyamide, 3-exo-(5-Isoxazol-3-yl-thiophene-2-sulfonylamino)-8-
oxa-bicyclo[3.2.1]octane-3-carboxylic acid hydroxyamide,
and 3-exo-(5-Phenylthiophene-2-sulfonylamino)-8-
oxabicyclo[3.2.1]octane-3-carboxylic acid hydroxyamide.

The present invention also relates to a pharmaceutical composition for the treatment of a condition selected from the group consisting of arthritis (including osteoarthritis and rheumatoid arthritis), inflammatory bowel disease, Crohn's disease, emphysema, chronic obstructive pulmonary disease, Alzheimer's disease, organ transplant toxicity, cachexia, allergic reactions, allergic contact hypersensitivity, cancer (such as solid tumor cancer including colon cancer breast cancer, lung cancer and prostrate cancer and hematopoietic malignancies including leukemias and lymphomas), tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neurodegenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis, septic shock and other diseases characterized by metalloproteinase activity and other diseases characterized by mammalian reprolysin activity in a mammal, including a human, comprising an amount of a compound of formula I or a pharmaceutically acceptable salt thereof effective in such treatments and a pharmaceutically acceptable carrier.

The present invention also relates to a pharmaceutical composition for the inhibition of (a) matrix metalloproteinases or other metalloproteinases involved in matrix degradation, or (b) a mammalian reprolysin (such as aggrecanase or ADAM's TS-1, 10, 12, 15 and 17, most preferably ADAM-17) in a mammal, including a human, comprising an effective amount of a compound of formula I or a pharmaceutically acceptable salt thereof.

The present invention also relates to a method for treating a condition selected from the group consisting of arthritis (including osteoarthritis and rheumatoid arthritis, inflammatory bowel disease. Crohn's disease, emphysema, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis, setic shock and other diseases characterized by metalloproteinase activity and other diseases characterized by mammalian reprolysin activity in a mammal, including a human, comprising administering to said mammal an amount of a compound of formula I or a pharmaceutically acceptable salt thereof effective in treating such a condition.

The present invention also relates to a method for the inhibition of (a) matrix metalloproteinases or other metalloproteinases involved in matrix degradation, or (b) a mammalian reprolysin (such as aggrecanase or ADAM's TS-1, 10, 12, 15 and 17, preferably ADAM-17) in a mammal, including a human, comprising administering to said mammal an effective amount of a compound of formula I or a pharmaceutically acceptable salt thereof.

This invention also encompasses pharmaceutical compositions containing prodrugs of compounds of the formula I. This invention also encompasses methods of treating or preventing disorders that can be treated or prevented by the inhibition of matrix metalloproteinases or the inhibition of mammalian reprolysin comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, omithine and methionine sulfone. Prodrugs also include compounds wherein carbonates, carbamates, amides and alkyl esters which are covalently bonded to the above substituents of formula I through the carbonyl carbon prodrug sidechain.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies and TNF receptor immunoglobulin molecules (such as Enbrel®), low dose methotrexate, lefunimide, hydroxychloroquine, d-pencilamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin. COX-2 inhibitors such as celecoxib and rofecoxib, analgesics and intraarticular therapies such as corticosteroids and hyaluronic acids such as hyalgan and synvisc.

The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine, and antimetabolites such as methotrexate.

The compounds of the present invention may also be used in combination with cardiovascular agents such as calcium channel blockers, lipid lowering agents such as statins, fibrates, beta-blockers, Ace inhibitors, Angiotensin-2 receptor antagonists and platelet aggregation inhibitors.

The compounds of the present invention may also be used in combination with CNS agents such as antidepressants (such as sertraline), anti-Parkinson drugs (such as deprenyl, L-dopa, requip, miratex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as Aricept, tacrine, COX-2 inhibitors, propentofylline or metryfonate.

The compounds of the present invention may also be used in combination with osteoporosis agents such as droloxifene or fosomax and immunosuppressant agents such as FK-506 and rapamycin.

DETAILED DESCRIPTION OF THE INVENTION

The following reaction Schemes illustrate the preparation of the compounds of the present invention. Unless otherwise indicated n, $R^1$, $R^2$, Q and Z in the reaction Schemes and the discussion that follow are defined as above.

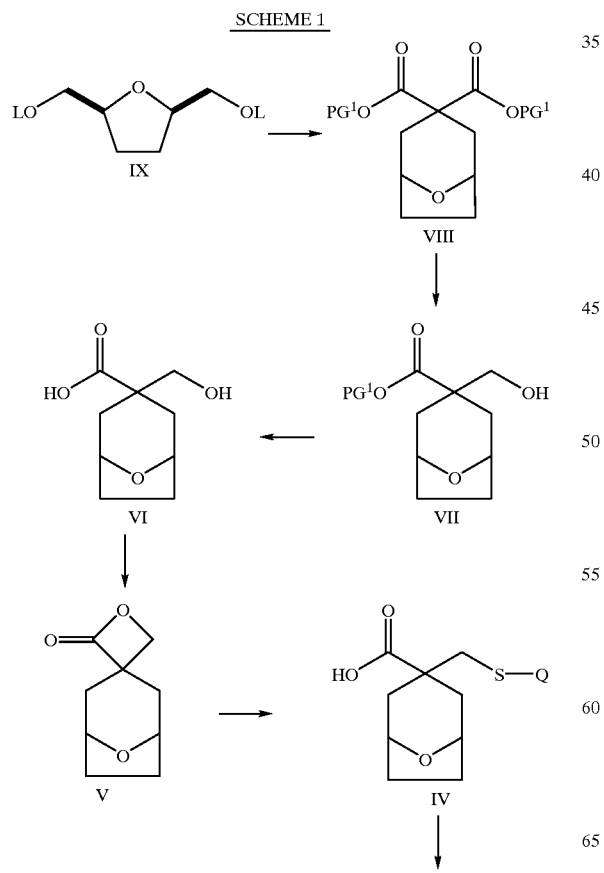

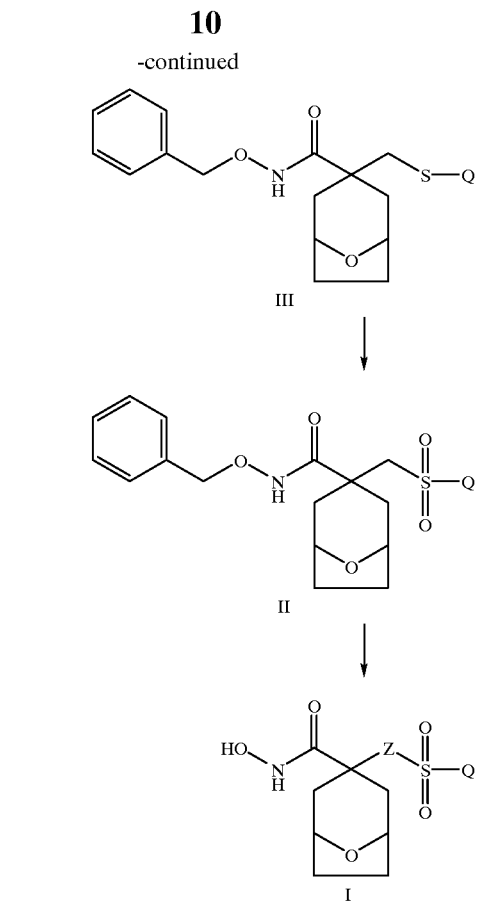

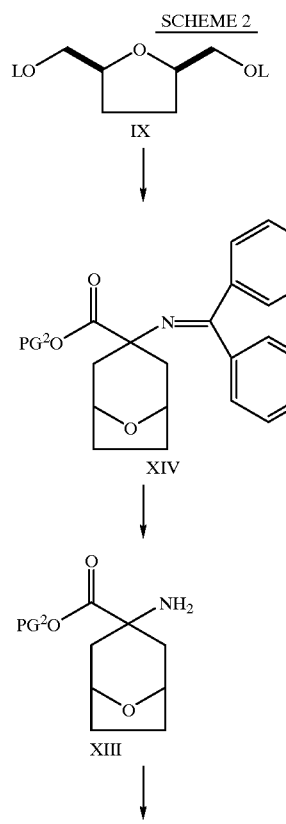

11
-continued
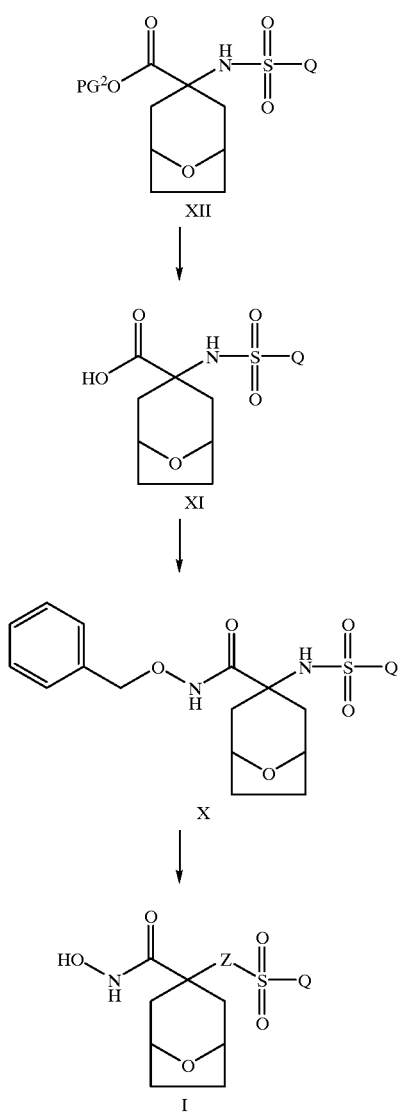
12
-continued
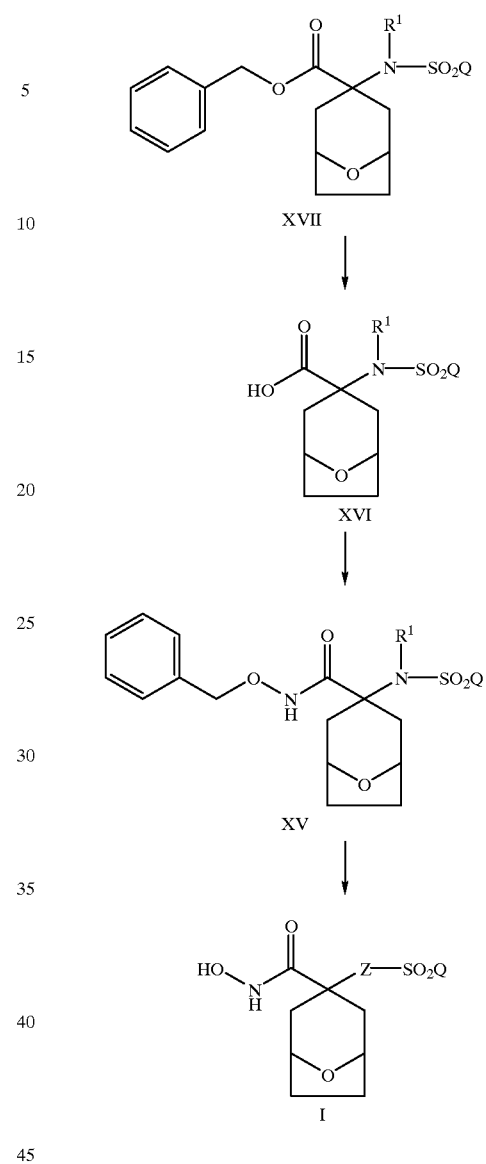
SCHEME 3
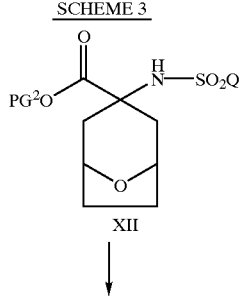
SCHEME 4
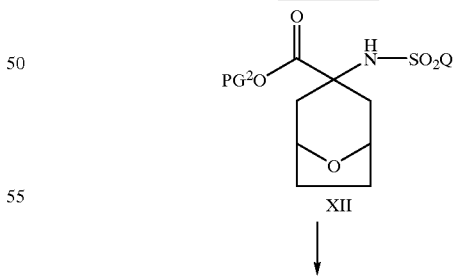

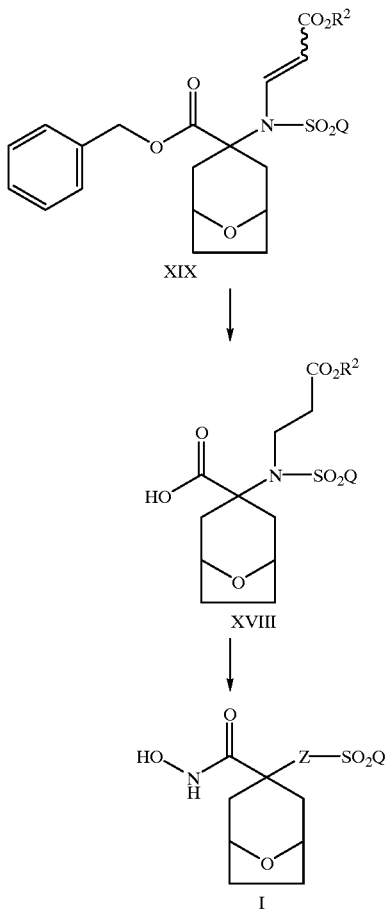

Scheme 1 refers to the preparation of compounds of formula I, wherein Z is $CH_2$. Referring to Scheme 1, a compound of formula I is prepared from a compound of the formula II by hydrogenolysis under an atmosphere of hydrogen in the presence of a catalyst in a reaction inert solvent. Suitable catalysts include 5% palladium on barium sulfate or 5% palladium on carbon, preferably 5% palladium on barium sulfate. Suitable solvents include an alcohol such as ethanol, methanol or isopropanol, preferably methanol. The aforesaid reaction may be performed at a pressure from about 1 to about 5 atmospheres, preferably about 3 atmospheres. Suitable temperatures for the aforesaid reaction range from about 20° C. (room temperature) to about 60° C., preferably the temperature may range from about 20° C. to about 25° C. (i.e. room temperature). The reaction is complete within about 0.5 hours to about 5 hours, preferably about 3 hours.

Compounds of the formula II can be prepared from compounds of the formula III by reaction with an oxidant in a reaction inert solvent. Suitable oxidants include meta-chloroperbenzoic acid, hydrogen peroxide or sodium perborate, preferably meta-chloroperbenzoic acid. Suitable solvents include halogenated solvents such as methylene chloride or chloroform, preferably methylene chloride. Suitable temperatures for the aforesaid reaction range from about 0° C. to about 60° C., preferably the temperature may range from about 20° C. to about 25° C. (i.e. room temperature). The reaction is complete within about 0.5 hours to about 24 hours, preferably about 16 hours.

The compound of formula III is prepared from a compound of formula IV by reaction with O-benzylhydroxyamine hydrochloride, an activating agent, and a base in a reaction inert solvent. Suitable activating agents include (benzotriazol-1-yloxy)tris(dimethylamino) phosphonium hexafluorophosphate or 1-(3-(dimethylaminopropyl)-3-ethylcarbodiimide hydrochloride, preferably (benzotriazol-1-yloxy)tris(dimethylamino) phosphonium hexafluorophosphate. Suitable bases include tertiary amines such as triethylamine, diisopropylethylamine or 4-N,N-dimethylaminopyridine, preferably diisopropylethylamine. The temperature of the aforesaid reaction may range from about 0° C. to about 60° C., preferably about 50° C. Suitable solvents include N,N-dimethylformamide, halogenated solvents such as methylene chloride or chloroform, or ethers such as THF or diethyl ether; preferably the solvent is N,N-dimethylformamide. The reaction is complete in about 4 hours to about 48 hours, preferably about 16 hours.

Compounds of the formula IV, can be prepared from compounds of the formula V, by reaction with a compound of the formula QSH, wherein Q is as defined above, in the presence of a strong base in an aprotic polar solvent. Suitable bases include sodium hydride, lithium diisopropylamide, potassium t-butoxide, sodium amide or potassium hydride, preferably sodium hydride. Suitable solvents include ethers (such as THF, diethyl ether or 1,2-dimethoxyethane), dimethoxyethane), or N,N-dimethylformamide, preferably the solvent is THF. The aforesaid reaction is conducted at about −78° C. to about 0° C., preferably at about 22° C. (i.e., room temperature) for a period of 30 minutes to about 24 hours, preferably about 2 hours.

Compounds of the formula V are prepared from compounds of the formula VI by dehydration in the presence of a tertiary amine base, preferably triethylamine, optionally in the presence of 4-dimethylaminopyridine, and a dehydrating agent in an inert solvent. Suitable dehydrating agents include trifluoromethanesulfonic anhydride, methanesulfonic anhydride, methanesulfonyl chloride, p-toluenesulfonyl chloride or benzenesulfonyl chloride, preferably benzenesulfonyl chloride. Suitable solvents include diethyl ether or dichloromethane. The reaction is performed at a temperature from about −80° C. to about 0° C., preferably about 0° C. The reaction is carried out for about 10 minutes to 4 hours, preferably about 1 hour.

The compounds of the formula VI are prepared from a compound of formula VII, wherein $PG^1$ is methyl or ethyl, by saponification with a base, such as lithium hydroxide, in a solvent mixture. Suitable solvent mixtures include water and methanol or water, methanol and THF. The reaction is performed at a temperature from about 60° C. to about 120° C., preferably at about the reflux temperature of the solvent mixture used. The reaction is carried out for about 30 minutes to 24 hours, preferably about 16 hours.

The exo-hydroxymethyl isomer of the compound of the formula VII is prepared from a compound of formula VIII. In general, a solution of a compound of formula VIII is dissolved in an inert aromatic solvent, preferably benzene or toluene, and cooled at about −40° C. to −20° C., preferably about −40° C. To the cold solution is added a suitable hindered reducing agent, preferably disobutylaluminum hydride, in an inert aromatic solvent, maintaining the temperature below −25° C. After the addition is complete, the reaction is maintained below 0° C. for about 3 hours. At about −15° C., a protic solvent, preferably ethanol, is added. After stirring at about −15° C. for about 1 hour, sodium borohydride is added and the reaction is allowed to warm to about room temperature while stirring for a period of 2 to 24 hours, preferably about 16 hours.

The endo-hydroxymethyl isomer of the compound of the formula VII can be prepared from the exo-hydroxymethyl compound of the formula VI by a series of steps which can invert the sterochemistry about the carbon atom bearing the hydroxymethyl and carboxylic acid groups. Specifically, the exo-hydroxymethyl isomer of formula VI is first converted to the corresponding benzyl ester. Subsequent Jones oxidation of the alcohol to the carboxylic acid and alkyl ester formation (methyl or ethyl) provides an intermediate mixed benzyl alkyl ester (i.e. the exo ester is methyl or ethyl and the endo ester is benzyl). The benzyl ester is then removed by hydrogenolysis and the resulting carboxylic acid is reduced to the alcohol by diborane reduction, providing the endo-hydroxymethyl isomer of the compound of the formula VII.

The compounds formula VIII, wherein $PG^1$ is ethyl or methyl, are prepared from compounds of the formula IX, wherein L is methanesulfonyl, benzensulfonyl or tosyl, by reaction with dimethyl or diethyl malonate in the presence of a strong base, such as sodium hydride, in a polar solvent, such as N,N-dimethylformamide, for a time period between about 4 hours to about 24 hours, preferably about 16 hours. The aforesaid reaction temperature is between about 70° C. to about 150° C., preferably about 140° C.

Compounds of the formula IX are known or can be made by methods well known to those of ordinary skill in the art.

Compounds of the formula QSH can be prepared by reaction of an alkyl or aryl halide with sodium sulfhydride as described in Jerry March, *Advanced Organic Chemistry*, 360 and 589 (3rd ed., 1985). Alternatively, compounds of the formula QSH can also be prepared by reaction of an aryl diazonium salt with sodium sulfhydride as described in March id. at 601. Alternatively, compounds of the formula QSH can also be prepared by reaction of a Grignard reagent with sulfur as described in March id. at 550. Alternatively, compounds of the formula QSH can also be prepared by reduction of a sulfonyl chloride, sulfonic acid or disulfide as described in March id. at 1107 and 1110.

Scheme 2 refers to the preparation of compounds of the formula I, wherein Z is $>NR^1$, and $R^1$ as hydrogen. Referring to Scheme 2, compounds of formula I can be prepared from compounds of the formula X by hydrogenolysis under an atmosphere of hydrogen in the presence of a catalyst in a reaction inert solvent. Suitable catalysts include 5% palladium on barium sulfate or 5% palladium on carbon, preferably 5% palladium on barium sulfate. Suitable solvents include an alcohol such as ethanol, methanol or isopropanol, preferably methanol. The aforesaid reaction may be performed at a pressure from about 1 to about 5 atmospheres, preferably about 3 atmospheres. Suitable temperatures for the aforesaid reaction range from about 20° C. (room temperature) to about 60° C., preferably the temperature may range from about 20° C. to about 25° C. (i.e. room temperature). The reaction is complete within about 0.5 hours to about 5 hours, preferably about 3 hours.

The compound of formula X is prepared from a compound of the formula XI by reaction with O-benzylhydroxylamine hydrochloride in the presence of a catalyst and a base in a reaction inert solvent. Suitable catalyst include (benzotriazol-1-yloxy)tris(dimethylamino) phosphonium hexafluorophosphate or 1-(3-(dimethylaminopropyl)-3-ethylcarbodiimide hydrochloride, preferably (benzotriazol-1-yloxy)tris(dimethylamino) phosphonium hexafluorophosphate. Suitable bases include tertiary amines such as triethylamine, diisopropylethylamine or 4-N,N-dimethylaminopyridine, preferably diisopropylethylamine. The aforesaid reaction temperature is from about 0° C. to about 60° C., preferably about 50° C. Suitable solvents include N,N-dimethylformamide or halogenated solvents such as methylene chloride or chloroform; preferably, the solvent is N,N-dimethylformamide. The reaction is conducted over a period of about 4 hours to about 48 hours, preferably about 16 hours.

Compounds of the formula XI are prepared from compounds of the formula XII, wherein $PG^2$ is methyl or ethyl, by saponification with a base such as sodium hydroxide in a solvent mixture such as water and ethanol. The reaction is performed at a temperature from about 60° C. to about 100° C., preferably at about the reflux temperature of the solvent mixture used. The reaction is carried out for about 1 day to 10 days, preferably about 6 days.

The compounds of the formula XII, wherein $PG^2$ is methyl or ethyl, are prepared from compounds of the formula XIII, wherein $PG^2$ is methyl or ethyl, by reaction with a compound of the formula $QSO_2Cl$ in the presence of a base, such as triethylamine, and a polar solvent. Suitable solvents include N,N-dimethylformamide, tetrahydrofuran, 1,2-dimethoxyethane, dioxane, water or acetonitrile, preferably N,N-dimethylformamide. The reaction mixture is stirred at room temperature for a time period between about 1 hour to about 24 hours, preferably about 16 hours.

Compounds of the formula XIII, wherein $PG^2$ is methyl or ethyl, are prepared from compounds of the formula XIV, wherein $PG^2$ is methyl or ethyl, by hydroylsis in the presence of aqueous mineral acid and a solvent such as diethyl ether. Suitable mineral acids include hydrochloric and sulfuric acid, preferably hydrochloric acid. The reaction is carried out at a temperature ranging from about 0° C. to 50° C.; preferably the temperature may range from about 20° C. to about 25° C. (i.e. room temperature). The reaction is conducted over a period of about 2 hours to about 48 hours, preferably about 16 hours.

Compounds of the formula XIV, wherein $PG^2$ is methyl, ethyl or benzyl, are prepared from compounds of the formula IX, wherein L is methanesulfonyl, benzenesulfonyl or tosyl, by reaction with N-diphenylmethylene glycine, methyl, ethyl or benzyl ester, in the presence of a strong base, such as sodium hydride, in a polar solvent, such as N,N-dimethylformamide, for a time period between about 4 hours to about 24 hours, preferably about 16 hours. The aforesaid reaction temperature is between about 70° C. to about 140° C., preferably about 100° C. Compounds of the formula XIV, wherein $PG^2$ is methyl, ethyl or benzyl, are obtained as mixtures of diastereomers which can be separated by chromatographic means.

Compounds of the formula $QSO_2Cl$ and formula IX are known or commercially available or can be made by methods well known to those of ordinary skill in the art.

Scheme 3 refers to the preparation of compounds of the formula I, wherein Z is $NR^1$ and $R^1$ is $(C_1-C_6)$ alkyl, $(C_6-C_{10})$ aryl$(C_1-C_6)$ alkyl, $(C_2-C_9)$heteroaryl$(C_1-C_6)$alkyl or a group of the formula $-(CH_2)_nCO_2R^2$, wherein n is 1, 3, 4, 5, or 6 and $R^2$ is $(C_1-C_6)$alkyl.

Referring to Scheme 3, compounds of the formula I, wherein Z is $NR^1$ and $R^1$ is $(C_1-C_6)$alkyl, $(C_6-C_{10})$aryl $(C_1-C_6)$alkyl, $(C_2-C_9)$heteroaryl$(C_1-C_6)$alkyl or a group of the formula $-(CH_2)_nCO_2R^2$, wherein n is 1, 3, 4, 5, or 6 and $R^2$ is $(C_1-C_6)$alkyl, are prepared from compounds of the formula XV by hydrogenolysis under an atmosphere of hydrogen in the presence of a catalyst in a reaction inert solvent. Suitable catalysts include 5% palladium on barium sulfate or 5% palladium on carbon, preferably 5% palladium on barium sulfate. Suitable solvents include an alcohol such as ethanol, ethanol or isopropanol, preferably methanol. The aforesaid reaction may be performed at a pressure from about 1 to about 5 atmospheres, preferably about 3 atmospheres. Suitable temperatures for the aforesaid reaction range from about 20° C. (room temperature) to about 60° C., preferably the temperature may range from about 20° C. to about 25° C. (i.e. room temperature). The reaction is complete within about 0.5 hours to about 5 hours, preferably about 3 hours.

The compound of formula XV is prepared from a compound of the formula XVI by reaction with O-benzylhydroxylamine hydrochloride in the presence of a catalyst and a base in a reaction inert solvent. Suitable catalyst include (benzotriazol-1-yloxy)tris(dimethylamino) phosphonium hexafluorophosphate or 1-(3-(dimethylaminopropyl)-3-ethylcarbodiimide hydrochloride, preferably (benzotriazol-1-yloxy)tris(dimethylamino) phosphonium hexafluorophosphate. Suitable bases include tertiary amines such as triethylamine, diisopropylethylamine or 4-N,N-dimethylaminopyridine, preferably diisopropylethylamine. The aforesaid reaction temperature is from about 0° C. to about 60° C. preferably about 50° C. Suitable solvents include N,N-dimethylformamide or halogenated solvents such as methylene chloride or chloroform, preferably the solvent is N,N-dimethylformamide. The reaction is conducted over a period of about 4 hours to about 48 hours, preferably about 16 hours.

The compound of formula XVI is prepared from a compound of the formula XVII by removal of the benzyl protecting group. Specifically, the benzyl protecting group is removed by hydrogenolysis using palladium or palladium on carbon in a solvent such as methanol or ethanol, for a period from which 30 minutes to about 48 hours, preferably 16 hours, at a temperature of about 20° C. to about 25° C. (i.e., room temperature).

The compound of formula XVII is prepared from a compound of the formula XII, wherein $PG^2$ is benzyl, by reaction with a reactive derivative of an alcohol of the formula $R^1OH$ such as the methanesulfonate, tosylate, chloro, bromo or iodo derivative, preferably the iodo derivative, in the presence of a base such as potassium carbonate or sodium hydride, preferably sodium hydride, and a polar solvent, such as N,N-dimethylformamide. The reaction mixture is stirred at room temperature for a time period between about 60 minutes to about 48 hours, preferably about 16 hours.

The compounds of formula XII, wherein $PG^2$ is benzyl, are prepared according to the methods of Scheme 2.

Scheme 4 refers to the preparation of compounds of formula I, wherein Z is $>NR^1$, $R^1$ is a group of the formula —$(CH_2)_2CO_2R^2$ (i.e. n is 2) and $R^2$ is $(C_1-C_6)$alkyl.

Referring to Scheme 4, compounds of said formula I are prepared from compounds of the formula XVIII, wherein $R^2$ is $(C_1-C_6)$alkyl, by reaction with oxalyl chloride or thionyl chloride, preferably oxalyl chloride, and a catalyst, preferably about 2% of N,N-dimethylformamide, in an inert solvent, such as methylene chloride, to form an in situ acid chloride that is subsequently reacted with O-trimethylsilylhydroxylamine in the presence of a base, such as pyridine, 4-N,N-dimethylaminopyridine or triethylamine, preferably pyridine. The reaction is performed at a temperature of about 22° C. (i.e., room temperature for about 1 to about 12 hours, preferably about 1 hour.

Compounds of the formula XVIII, wherein $R^2$ is $(C_1-C_6)$ alkyl, can be prepared from compounds of the formula XIX, wherein $R^2$ is $(C_1-C_6)$alkyl, by reduction in a polar solvent. Suitable reducing agents include hydrogen over palladium and hydrogen over palladium on carbon, preferably hydrogen over palladium on carbon. Suitable solvents include methanol, ethanol and isopropanol, preferably ethanol. The aforesaid reaction is performed at a temperature of about 22° C. (i.e., room temperature) for a period of 1 to 7 days, preferably about 2 days.

Compounds of the formula XIX, wherein $R^2$ is $(C_1-C_6)$ alkyl, can be prepared from compounds of the formula XII, wherein $PG^2$ is benzyl, by Michael addition of a propiolate ester and a base in a polar solvent. Suitable propiolates are of the formula H—C≡C—$CO_2R^2$, wherein $R^2$ is $(C_1-C_6)$ alkyl. Suitable bases include tetrabutylammonium fluoride, potassium carbonate, and cesium carbonate, preferably tetrabutylammonium fluoride. Suitable solvents include tetrahydrofuran, acetonitrile, tert-butanol and N,N-dimethylformamide, preferably tetrahydrofuran. The aforesaid reaction is performed at a temperature of about −10° C. to about 60° C., preferably ranging between 0° C. and about 22° C. (i.e., room temperature). The compounds of formula XIX are obtained as mixtures of geometric isomers about the olefinic double bond; separation of the isomers is not necessary.

Compounds of the formula XII, wherein $PG^2$ is benzyl, can be prepared according to the methods of Scheme 2.

Compounds of said formula I, wherein Z is $>NR^1$, $R^1$ is a group of the formula —$(CH_2)_nCO_2R^2$, n is 1 to 6 and $R^2$ is hydrogen are prepared from compounds of formula I, wherein Z is $>NR^1$, $R^1$ is a group of the formula —$(CH_2)_nCO_2R^2$, n is 1 to 6 and $R^2$ is $(C_1-C_6)$alkyl, by saponification using a base such as sodium hydroxide in a protic solvent such as ethanol, methanol or water or a mixture such as water and ethanol, water and toluene, or water and THF. The preferred solvent system is water and ethanol. The reaction is conducted for a period of 30 minutes to 24 hours, preferably about 2 hours.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmaceutically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, are capable of forming base salts with various pharmaceutically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmaceutically acceptable cations as sodium, potassium, calcium and magnesium, etc. These salts can easily be prepared by treating the corresponding acidic compounds with an aqueous solution containing the desired pharmaceutically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields. The ability of the compounds of formula I or their pharmaceutically acceptable salts (hereinafter also referred to as the compounds of the present invention) to inhibit metalloproteinases or mammalian reprolysin and, consequently, demonstrate their effectiveness for treating diseases characterized by metalloproteinase or the production of tumor necrosis factor is shown by the following in vitro assay tests.

Biological Assay

Inhibition of Human Collagenase (MMP-1)

Human recombinant collagenase is activated with trypsin. The amount of trypsin is optimized for each lot of collagenase-1 but a typical reaction uses the following ratio: 5 μg trypsin per 100 μg of collagenase. The trypsin and collagenase are incubated at room temperature for 10 minutes then a five fold excess (50 mg/10 mg trypsin) of soybean trypsin inhibitor is added.

Stock solutions (10 mM) of inhibitors are made up in dimethylsulfoxide and then diluted using the following scheme:

10 mM→120 μM→12 μM→1.2 μM→0.12 μM

Twenty-five microliters of each concentration is then added in triplicate to appropriate wells of a 96 well microfluor plate. The final concentration of inhibitor will be a 1.4 dilution after addition of enzyme and substrate. Positive controls (enzyme, no inhibitor) are set up in wells D7–D12 and negative controls (no enzyme, no inhibitors) are set in wells D1–D6.

Collagenase-1 is diluted to 240 ng/ml and 25 ml is then added to appropriate wells of the microfluor plate. Final concentration of collagenase in the assay is 60 ng/ml.

Substrate (DNP-Pro-Cha-Gly-Cys(Me)-His-Ala-Lys (NMA)-NH$_2$) is made as a 5 mM stock in dimethylsulfoxide and then diluted to 20 μM in assay buffer. The assay is initiated by the addition of 50 ml substrate per well of the microfluor plate to give a final concentration of 10 mM.

Fluorescence reading (360 nM excitation, 460 nm emission) are taken at time 0 and then at 20 minute intervals. The assay is conducted at room temperature with a typical assay time of 3 hours Fluorescence versus time is then plotted for both the blank and collagenase containing samples (data from triplicate determinations is averaged). A time point that provides a good signal (at least five fold over the blank) and that is on a linear part of the curve (usually around 120 minutes) is chosen to determine IC$_{50}$ values. The zero time is used as a blank for each compound at each concentration and these values are subtracted from the 120 minute data. Data is plotted as inhibitor concentration versus % control (inhibitor fluorescence divided by fluorescence of collagenase alone× 100). IC$_{50}$'s are determined from the concentration of inhibitor that gives a signal that is 50% of the control.

If IC$_{50}$'s are reported to be less than 0.03 nM then the inhibitors are assayed at concentrations of 0.3 mM, 0.03 mM, and 0.003 mM.

Inhibition of Gelatinase (MMP-2)

Human recombinant 72 kD gelatinase (MMP-2, gelatinase A) is activated for 16–18 hours with 1 mM p-aminophenyl-mercuric acetate (from a freshly prepared 100 mM stock in 0.2 N NaOH) at 4° C., rocking gently.

10 mM dimethylsulfoxide stock solutions of inhibitors are diluted serially in assay buffer (50 mM TRIS, pH 7.5, 200 mM NaCl, 5 mM CaCl$_2$, 20 μM ZnCl$_2$ and 0.02% BRIJ-35 (vol./vol.)) using the following scheme:

10 mM→120 μM→12 μM→1.2 μM→0.12 μM

Further dilutions are made as necessary following this same scheme. A minimum of four inhibitor concentrations for each compound are performed in each assay. 25 μL of each concentration is then added to triplicate wells of a black 96 well U-bottomed microfluor plate. As the final assay volume is 100 μL, final concentrations of inhibitor are the result of a further 1:4 dilution (i.e. 30 μM→3 μM→0.3 μM→0.03 μM, etc.). A blank (no enzyme, no inhibitor) and a positive enzyme control (with enzyme, no inhibitor) are also prepared in triplicate.

Activated enzyme is diluted to 100 ng/mL in assay buffer, 25 μL per well is added to appropriate wells of the microplate. Final enzyme concentration in the assay is 25 ng/mL (0.34 nM).

A five mM dimethylsulfoxide stock solution of substrate (Mca-Pro-Leu-Gly-Leu-Dpa-Ala-Arg-NH$_2$) is diluted in assay buffer to 20 μM. The assay is initiated by addition of 50 μL of diluted substrate yielding a final assay concentration of 10 μM substrate. At time zero, fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for IC$_{50}$ determinations. The zero time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. IC$_{50}$'s are defined as the concentration of inhibitor that gives a signal that is 50% of the positive enzyme control.

Inhibition of Stromelysin Activity (MMP-3)

Human recombinant stromelysin (MMP-3, stromelysin-1) is activated for 20–22 hours with 2 mM p-aminophenyl-mercuric acetate (from a freshly prepared 100 mM stock in 0.2 N NaOH) at 37° C.

10 mM dimethylsulfoxide stock solutions of inhibitors are diluted serially in assay buffer (50 mM TRIS, pH 7.5, 150 mM NaCl, 10 mM CaCl$_2$ and 0.05% BRIJ-35 (vol./vol.)) using the following scheme:

10 mM→120 μM→12 μM→1.2 μM→0.12 μM

Further dilutions are made as necessary following this same scheme. A minimum of four inhibitor concentrations for each compound are performed in each assay. 25 μL of each concentration is then added to triplicate wells of a black 96 well U-bottomed microfluor plate. As the final assay volume is 100 μL, final concentrations of inhibitor are the result of a further 1:4 dilution (i.e. 30 μM→3 μM→0.3 μM→0.03 μM, etc.). A blank (no enzyme, no inhibitor) and a positive enzyme control (with enzyme, no inhibitor) are also prepared in triplicate.

Activated enzyme is diluted to 200 ng/mL in assay buffer, 25 μL per well is added to appropriate wells of the microplate. Final enzyme concentration in the assay is 50 ng/mL (0.875 nM).

A ten mM dimethylsulfoxide stock solution of substrate (Mca-Arg-Pro-Lys-Pro-Val-Glu-Nva-Trp-Arg-Lys(Dnp)-NH$_2$) is diluted in assay buffer to 6 μM. The assay is initiated by addition of 50 μL of diluted substrate yielding a final assay concentration of 3 μM substrate. At time zero, fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for IC$_{50}$ determinations. The zero time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. IC$_{50}$'s are defined as the concentration of inhibitor that gives a signal that is 50% of the positive enzyme control.

Alternatively, inhibition of stromelysin activity can be assayed using Mca-Arg-Pro-Lys-Pro-Val-Glu-Nva-Trp-Arg-Lys(Dnp)-NH$_2$ (3 μM) under conditions similar as in inhibition of human collagenase (MMP-1).

Human stromelysin is activated for 20–24 hours at 37° C. with 2 mM APMA (p-aminophenyl mercuric acetate) and is diluted to give a final concentration in the assay of 50 ng/ml. Inhibitors are diluted as for inhibition of human collagenase (MMP-1) to give final concentrations in the assay of 30 μM, 3 μM, 0.3 μM, and 0.03 μM. Each concentration is done in triplicate.

Fluorescence readings (320 nm excitation, 390 emission) are taken at time zero and then at 15 minute intervals for 3 hours.

IC$_{50}$'s are determined as per inhibition of human collagenase (MMP-1). If IC$_{50}$'s are reported to be less than 0.03 μM, then the inhibitors are assay at final concentrations of 0.03 μM, 0.003 μM, 0.0003 μM, and 0.00003 μM.

IC$_{50}$ values were determined in the same manner as for collagenase.

Inhibition of MMP-13

Human recombinant MMP-13 is activated with 2 mM APMA (p-aminophenyl mercuric acetate) for 2.0 hours, at 37° C. and is diluted to 240 ng/ml in assay buffer (50 mM Tris, pH 7.5, 200 mM sodium chloride, 5 mM calcium chloride, 20 mM zinc chloride, 0.02% brij 35). Twenty-five microliters of diluted enzyme is added per well of a 96 well microfluor plate. The enzyme is then diluted in a 1:4 ratio in the assay by the addition of inhibitor and substrate to give a final concentration in the assay of 60 ng/ml.

Stock solutions (10 mM) of inhibitors are made up in dimethylsulfoxide and then diluted in assay buffer as per the inhibitor dilution scheme for inhibition of human collagenase-1 (MMP-1): Twenty-five microliters of each concentration is added in triplicate to the microfluor plate. The final concentrations in the assay are 30 mM, 3 mmM, 0.3 m mM, and 0.03 mmM.

Substrate (Dnp-Pro-Cha-Gly-Cys(Me)-His-Ala-Lys(NMA)-NH$_2$) is prepared as for inhibition of human collagenase (MMP-1) and 50 μl is added to each well to give a final assay concentration of 10 μM. Fluorescence readings (360 nM excitation; 450 nM emission) are taken at time 0 and every 5 minutes for 1 hour.

Positive controls and negative controls are set up in triplicate as outlined in the MMP-1 assay.

IC$_{50}$'s are determined as per inhibition of human collagenase (MMP-1). If IC$_{50}$'s are reported to be less than 0.03 mM, inhibitors are then assayed at final concentrations of 0.03 mM, 0.03 mmM, 0.003 mmM, and 0.0003 mM.

Inhibition of TNF Production

The ability of the compounds or the pharmaceutically acceptable salts thereof to inhibit the production of TNF and, consequently, demonstrate their effectiveness for treating diseases involving the production of TNF is shown by the following in vitro assay:

Human mononuclear cells were isolated from anti-coagulated human blood using a one-step Ficoll-hypaque separation technique. (2) The mononuclear cells were washed three times in Hanks balanced salt solution (HBSS) with divalent cations and resuspended to a density of 2× 10$^6$/ml in HBSS containing 1% BSA. Differential counts determined using the Abbott Cell Dyn 3500 analyzer indicated that monocytes ranged from 17 to 24% of the total cells in these preparations.

180 μl of the cell suspension was aliquoted into flat bottom 96 well plates (Costar). Additions of compounds and LPS (100 ng/ml final concentration) gave a final volume of 200 μl. All conditions were performed in triplicate. After a four hour incubation at 37° C. in an humidified CO$_2$ incubator, plates were removed and centrifuged (10 minutes at approximately 250×g) and the supermatans removed and assayed for TNFa using the R&D ELISA Kit.

Inhibition of Soluble TNF-α Production

The ability of the compounds or the pharmaceutically acceptable salts thereof to inhibit the cellular release of TNF-α and, consequently, demonstrate their effectiveness for treating diseases involving the disregulation of soluble TNF-α is shown by the following in vitro assay:

Method for the Evaluation of Recombinant TNF-α Converting Enzyme Activity

Expression of Recombinant TACE

A DNA fragment coding for the signal sequence, preprodomain, prodomain and catalytic domain of TACE (amino acids 1–473), can be amplified by polymerase chain reaction using a human lung cDNA library as a template. The amplified fragment is then cloned into pFastBac vector. The DNA sequence of the insert is confirmed for both the strands. A bacmid prepared using pFastBac in *E. coli* DH10Bac is transfected into SF9 insect cells. The virus particles is then amplified to P1, P2, P3 stages. The P3 virus is infected into both Sf9 and High Five insect cells and grown at 27° C. for 48 hours. The medium is collected and used for assays and further purification.

Preparation of Fluorescent Quenched Substrate

A model peptidic TNF-α substrate (LY-LeucineAlanineGlutamineAlanineValine-ArginineSerine-SerineLysine(CTMR)-Argine (LY=Lucifer Yellow; CTMR=Carboxytetramethyl-Rhodamine)) is prepared and the concentration estimated by absorbance at 560 nm ($E_{560}$, 60,000 M-1CM-1) according to the method of Goeghegan, KF, "Improved method for converting an unmodified peptide to an energy-transfer substrate for a proteinase." *Bioconjugate Chem.* 7, 385–391 (1995). This peptide encompasses the cleavage cite on pro-TNF which is cleaved in vivo by TACE.

Expression of Recombinant TACE

A DNA fragment coding for the signal sequence, preprodomain, prodomain and catalytic domain of TACE (amino acids 1–473), is amplified by polymerase chain reaction using a human lung cDNA library as a template. The amplified fragment is cloned into pFastBac vector. The DNA sequence of the insert is confirmed for both the strands. A bacmid prepared using pFastBac in *E. coli* DH10Bac is transfected into SF9 insect cells. The virus particles were amplified to P1, P2, P3 stages. The P3 virus is infected into both Sf9 and High Five insect cells and grown at 27° C. for 48 hours. The medium is collected and used for assays and further purification.

Enzyme Reaction

The reaction, carried out in a 96 well plate (Dynatech), is comprised of 70 μl of buffer solution (25 mM Hepes-HCl, pH7.5, plus 20 uM $ZnCl_2$), 10 μl of 100 μM fluorescent quenched substrate, 10 μl of a DMSO (5%) solution of test compound, and an amount of r-TACE enzyme which will cause 50% cleavage in 60 minutes—in a total volume of 100 μl. The specificity of the enzyme cleavage at the amide bond between alanine and valine is verified by HPLC and mass spectrometry. Initial rates of cleavage are monitored by measuring the rate of increase in fluorescence at 530 nm (excitation at 409 nm) over 30 minutes. The experiment is controlled as follows: 1) for background fluorescence of substrate; 2) for fluorescence of fully cleaved substrate; 3) for fluorescence quenching or augmentation from solutions containing test compound.

Data is analyzed as follows. The rates from the non-test compound containing "control" reactions were averaged to establish the 100% value. The rate of reaction in the presence of test compound was compared to that in the absence of compound, and tabulated as "percent of non-test compound containing control. The results are plotted as "% of control" vs. the log of compound concentration and a half-maximal point or $IC_{50}$ value determined.

All of the compounds of the invention have $IC_{50}$ of less than 1 μM, preferably less than 50 nM. Most preferred compounds of the invention are at least 100 fold less potent against r-MMP-1 than in the above TACE assay.

Human Monocyte Assay

Human mononuclear cells are isolated from anticoagulated human blood using a one-step Ficoll-hypaque separation technique. (2) The mononuclear cells are washed three times in Hanks balanced salt solution (HBSS) with divalent cations and resuspended to a density of $2\times10^6$/ml in HBSS containing 1% BSA. Differential counts determined using the Abbott Cell Dyn 3500 analyzer indicated that monocytes ranged from 17 to 24% of the total cells in these preparations.

180 m of the cell suspension was aliquoted into flat bottom 96 well plates (Costar). Additions of compounds and LPS (100 ng/ml final concentration) gave a final volume of 200 μl. All conditions were performed in triplicate. After a four hour incubation at 37° C. in an humidified $CO_2$ incubator, plates were removed and centrifuged (10 minutes at approximately 250×g) and the supermatants removed and assayed for TNF-α using the R&D ELISA Kit.

Aggrecanase Assay

Primary porcine chondrocytes from articular joint cartilage are isolated by sequential trypsin and collagenase digestion followed by collagenase digestion overnight and are plated at $2\times10^5$ cells per well into 48 well plates with 5 $\mu Ci/ml^{35}S$ (1000 Ci/mmol) sulphur in type I collagen coated plates. Cells are allowed to incorporate label into their proteoglycan matrix (approximately 1 week) at 37° C., under an atmosphere of 5% $CO_2$.

The night before initiating the assay, chondrocyte monolayers are washed two times in DMEM/1% PSF/G and then allowed to incubate in fresh DMEM/1% FBS overnight.

The following morning chondrocytes are washed once in DMEM/1% PSF/G. The final wash is allowed to sit on the plates in the incubator while making dilutions.

Media and dilutions can be made as described in the Table below.

| | |
|---|---|
| Control Media | DMEM alone (control media) |
| IL-1 Media | DMEM + IL-1 (5 ng/ml) |
| Drug Dilutions | Make all compounds stocks at 10 mM in DMSO. Make a 100 uM stock of each compound in DMEM in 96 well plate. Store in freezer overnight. The next day perform serial dilutions in DMEM with IL-1 to 5 uM, 500 nM, and 50 nM. Aspirate final wash from wells and add 50 ul of compound from above dilutions to 450 ul of IL-1 media in appropriate wells of the 48 well plates. Final compound concentrations equal 500 nM, 50 nM, and 5 nM. All samples completed in triplicate with Control and IL-1 alone samples on each plate. |

Plates are labeled and only the interior 24 wells of the plate are used. On one of the plates, several columns are designated as IL-1 (no drug) and Control (no IL-1, no drug). These control columns are periodically counted to monitor 35S-proteoglycan release. Control and IL-1 media are added to wells (450 ul) followed by compound (50 ul) so as to initiate the assay. Plates are incubated at 37° C., with a 5% $CO_2$ atmosphere.

At 40–50% release (when CPM from IL-1 media is 4–5 times control media) as assessed by liquid scintillation counting (LSC) of media samples, the assay is terminated (9–12 hours). Media is removed from all wells and placed in scintillation tubes. Scintillate is added and radioactive counts are acquired (LSC). To solubilize cell layers, 500 ul of papain digestion buffer (0.2 M Tris, pH 7.0, 5 mM EDTA, 5 mM DDT, and 1 mg/ml papain) is added to each well. Plates with digestion solution are incubated at 60° C. overnight. The cell layer is removed from the plates the next day and placed in scintillation tubes. Scintillate is then added, and samples counted (LSC).

The percent of released counts from the total present in each well is determined. Averages of the triplicates are made with control background subtracted from each well. The percent of compound inhibition is based on IL-1 samples as 0% inhibition (100% of total counts).

For administration to mammals, including humans, for the inhibition of matrix metalloproteinases or the production of tumor necrosis factor (TNF), a variety of conventional routes may be used including oral, parenteral (e.g., intravenous, intramuscular or subcutaneous), buccal, anal and topical. In general, the active compound will be administered at dosages between about 0.1 and 25 mg/kg body weight of the subject to be treated per day, preferably from about 0.3 to 5 mg/kg. Preferably the active compound will be administered orally or parenterally. However, some variation in dosage will necessarily occur depending on the condition of the subject being treated. The person responsible for administration will, in any event, determine the appropriate dose for the individual subject.

The compounds of the present invention can be administered in a wide variety of different dosage forms, in general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof. In the case of animals, they are advantageously contained in an animal feed or drinking water in a concentration of 5–5000 ppm, preferably 25 to 500 ppm.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. In the case of animals, compounds can be administered intramuscularly or subcutaneously at dosage levels of about 0.1 to 50 mg/kg/day, advantageously 0.2 to 10 mg/kg/day given in a single dose or up to 3 divided doses.

For topical ocular administration, direct application to the affected eye may be employed in the form of a formulation as eyedrops, aerosol, gels or ointments, or can be incorporated into collagen (such as poly-2-hydroxyethylmethacrylate and co-polymers thereof), or a hydrophilic polymer shield. The materials can also be applied as a contact lens or via a local reservoir or as a subconjunctival formulation.

For intraorbital administration a sterile injectable solution of the active ingredient is usually prepared. Solutions of a therapeutic compound of the present invention in an aqueous solution or suspension (particle size less than 10 micron) may be employed. The aqueous solutions should be suitable adjusted and buffered, preferably at a pH between 5 and 8, if necessary and the liquid diluent first rendered isotonic. Small amounts of polymers can be added to increase viscosity or for sustained release (such as cellulosic polymers, Dextran, polyethylene glycol, or alginic acid). These solutions are suitable for intraorbital injection purposes. The preparation of all these solutions under sterile conditions is readily accomplished by standard pharmaceutical techniques well known to those skilled in the art. In the case of animals, compounds can be administered intraorbitally at dosage levels of about 0.1 to 50 mg/kg/day, advantageously 0.2 to 10 mg/kg/day given in a single dose or up to 3 divided doses.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

The following Preparations and Examples illustrate the preparation of the compounds of the present invention. Melting points are uncorrected. NMR data are reported in parts per million (δ) and are referenced to the deuterium lock signal from the sample solvent (deuteriochloroform unless otherwise specified). Commercial reagents were utilized without further purification. THF refers to tetrahydrofuran. DMF refers to N,N-dimethylformamide. Chromatography refers to column chromatography performed using 32–63 mm silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure means that a rotary evaporator was used.

Preparation 1

4-(4-Fluorophenoxy)thiophenol

Lithium aluminum hydride (9.95 grams, 0.26 mole) was added in portions to a stirred solution of 4-(4- fluorophenoxy)benzenesulfonylchloride (30 grams, 0.105 mole) in tetrahydrofuran (700 mL). The resulting mixture was heated at reflux for 1.5 hours, cooled in an ice bath and quenched by addition of 10% aqueous sulfuric acid solution (100 mL). After stirring for 30 minutes, the mixture was filtered through Celite™ and the tetrahydrofuran was removed under vacuum. The residue was diluted with water and extracted with diethyl ether. The organic layer was washed with water and brine, dried over magnesium sulfate and concentrated under vacuum to provide the title compound as a white solid (23 grams, 100%).

Preparation 2

4'-Fluorobiphenyl-4-thiol

Lithium aluminum hydride (0.95 grams, 25 mmole) was added in portions to a stirred solution of 4'-fluorobiphenyl-4-sulfonylchloride (2.7 grams, 10 mmole) in tetrahydrofuran (75 mL). The resulting mixture was heated at reflux for 4 hours, cooled in an ice bath and quenched by addition of 10% aqueous sulfuric acid solution (100 mL). After stirring for 30 minutes, the mixture was filtered through Celite™ and the tetrahydrofuran was removed under vacuum. The residue was diluted with water and extracted with diethyl ether. The organic layer was washed with water and brine, dried over magnesium sulfate and concentrated under vacuum to a solid. Trituration of the solid with diethyl ether, removal of insoluble material by filtration and concentrated of the filtrate provided the title compound as a yellow solid (1.4 grams, 69%).

Preparation 3

4-(4-Chlorophenoxy)thiophenol

Lithium aluminum hydride (6.5 grams, 0.17 mole) was added in portions, maintaining gentle reflux, to a stirred solution of 4-chlorophenoxy)benzenesulfonyl-chloride (20.5 grams, 68 mmole) in tetrahydrofuran (400 mL). The resulting mixture was stirred at room temperature for 2 hours, cooled in an ice bath and quenched by addition of 10% aqueous sulfuric acid solution (100 mL). After stirring for 30 minutes, the mixture was diluted with water and extracted with diethyl ether. The organic layer was washed with water and brine, dried over magnesium sulfate and concentrated under vacuum to provide the title compound as a white solid (15.9 grams, 99%).

EXAMPLE 1

3-EXO-[4-(4-FLUOROPHENOXY) BENZENESULFONYLAMINO]-8-OXABICYCLO [3.2.1]-OCTANE-3-CARBOXYLIC ACID HYDROXYAMIDE

A) 3-(Benzhydrylideneamino)-8-oxabicyclo[3.2.1] octane-3-carboxylic Acid Ethyl Ester To a suspension of sodium hydride (0.41 grams, 17.1 mmole) in N,N-dimethylformamide (50 mL) at 0° C. was added dropwise a solution of N-diphenylmethylene glycine ethyl ester (2.07 grams, 7.8 mmol) in N,N-dimethylformamide (50 mL). After stirring for 30 minutes at room temperature, a solution of cis-2,5-bis(hydroxymethyl)-tetrahydrofuran ditosylate (4.1 grams, 9.3 mmole) in N,N-dimethylformamide (50 mL) was added dropwise. The reaction mixture was gradually heated to 100° C. in an oil bath and stirred at this temperature overnight. The solvent was evaporated under vacuum and the reside was taken up in water and extracted twice with diethyl ether. The combined organic extracts were washed with brine, dried over magnesium sulfate and concentrated to a brown oil, from which the title compound (1.42 grams, 51%, a 3:1 mixture of exo/endo diastereomers) was isolated by chromatography on silica gel (20% ethyl acetate in hexane as eluant).

B) 3-Amino-8-oxabicyclo[3.2.1]octane-3-carboxylic Acid Ethyl Ester Hydrochloride A two-phase mixture of 3-(benzhydrylideneamino)-8-oxabicyclo[3.2.1]octane-3-carboxylic acid ethyl ester (1.4 grams, 3.9 mmol) in aqueous 1N hydrochloric acid solution (100 mL) and diethyl ether (100 mL) was stirred at room temperature overnight. The aqueous layer was concentrated to provide the title compound (0.70 grams, 78%, a 3:1 mixture of exo/endo diastereomers) as a pale yellow solid.

C) 3-exo-[4-(4-Fluorophenoxy)benzenesulfonylamino]-8-oxabicyclo[3.2.1]octane-3-carboxylic acid ethyl ester A solution of 3-amino-8-oxabicyclo[3.2.1]octane-3-carboxylic acid ethyl ester hydrochloride (690 mg, 2.9 mmole), 4-(4-fluorophenoxy)benezenesulfonylchloride (923 mg, 3.2 mmole) and triethylamine (0.9 mL, 6.5 mmole) in N,N-dimethylformamide (45 mL) was stirred at room temperature overnight. The solvent was removed under vacuum and the residue was taken up in saturated aqueous sodium bicarbonate solution. After extracting twice with methylene chloride, the combined organic layers were washed with brine, dried over magnesium sulfate and concentrated to a brown oil. The title compound (492 mg, 38%) was isolated by chromatography on silica using 1% methanol in methylene chloride as eluant.

D) 3-exo-[4-(4-Fluorophenoxy)benzenesulfonylamino]-8-oxabicyclo[3.2.1]octane-3-carboxylic acid Sodium hydroxide (1.5 grams, 38 mmole) was added to a solution of 3-exo-[4-(4-fluorophenoxy) benzenesulfonylamino]-8-oxabicyclo[3.2.1]octane-3-carboxylic acid ethyl ester (492 mg, 1.09 mmole) in a mixture of ethanol (10 mL) and water (10 mL). The mixture was heated at reflux for 6 days, cooled and acidified with aqueous 1N hydrochloric acid solution. The mixture was extracted with ethyl acetate and the organic layer was washed with brine, dried over magnesium sulfate and concentrated to provide the title compound (411 mg, 89%) as a tan foam.

E) 3-exo-[4-(4-Fluorophenoxy)benzenesulfonylamino]-8-oxabicyclo[3.2.1]octane-3-carboxylic acid benzyloxyamide To a solution of 3-exo-[4-(4-fluorophenoxy) benzenesulfonylamino]-8-oxabicyclo-[3.2.1]octane-3-carboxylic acid (411 mg, 0.98 mmole) and triethylamine (0.19 mL, 1.36 mmole) in N,N-dimethylformamide (30 mL) was added (benzotriazol-1-yloxy)tris-(dimethylamino) phoshonium hexafluoroborate (474 mg, 1.07 mmole). After stirring at room temperature for 1 hour, additional triethylamine (0.22 mL, 1.58 mmole), and O-benzylhydroxylamine hydrochloride (187 mg, 1.17 mmole) were added. The reaction mixture was stirred for 1 day at room temperature and then for 1 day at 50° C. After concentration under vacuum, the residue was dissolved in ethyl acetate and washed sequentially with aqueous 1N hydrochloric acid solution, saturated aqueous sodium bicarbonate solution, and brine. The solution was dried over magnesium sulfate and concentrated to an oil from which the title compound, a white solid (237 mg, 46%) was isolated by chromatography (50% ethyl acetate in hexane as eluant).

F) 3-exo-[4-(4-Fluorophenoxy)benzenesulfonylamino]-8-oxa-bicyclo[3.2.1]octane-3-carboxylic acid hydroxyamide A solution of 3-exo-[4-(4-fluorophenoxy) benzenesulfonylamino]-8-oxabicyclo-[3.2.1]octane-3-carboxylic acid benzyloxyamide (237 mg, 0.45 mmole) in methanol (25 mL) was treated with 5% palladium on barium sulfate (150 mg) and hydrogenated at 3 atmospheres pressure for 4 hours in a Parr ™ shaker. The catalyst was removed by passage through a 0.45 μm nylon filter and the filtrate was concentrated to a white foam. Crystallization from methylene chloride provided the title compound as a white solid (62 mg, 32%). A second crop (62 mg, 32%) was obtained by crystallization from ethyl acetate/hexane.

M.p. 138°–141° C., $^1$H NMR (d$_6$-DMSO): δ 10.50 (br s, 1 H), 8.56 (br s, 1 H), 7.67 (d, J=8.7 Hz, 2 H), 7.66 (br s, 1 H, overlapped), 7.26–7.22 (m, 2 H), 7.16–7.12 (m, 2 H), 7.01 (d, J=8.5 Hz, 2 H), 4.09 (br s, 2 H), 2.32 (d, J=14.1 Hz, 2 H), 1.68–1.63 (m, 4 H), 1.51–1.48 (m, 2 H. MS: 435 m/e (M—H). Further confirmation of structure and stereochemistry was carried out by single crystal X-ray crystallography.

EXAMPLE 2

3-EXO-[4-(4-FLUOROPHENOXY) BENZENESULFONYLMETHYL]-8-OXABICYCLO-[3.2.1]-OCTANE-3-CARBOXYLIC ACID HYDROXYAMIDE

A) 8-Oxabicyclo[3.2.1]octane-3,3-dicarboxylic acid diethyl ester

Sodium hydride (2.28 grams, 95 mmole) was added in portions to a stirred solution of diethyl malonate (15 mL, 99 mmole) in N,N-dimethylformamide (400 mL). The mixture was stirred for 45 minutes at which time evolution of hydrogen was complete. A solution of cis-2,5-bis (hydroxymethyl)tetrahydrofuran ditosylate (19.0 grams, 43 mmole) in N,N-dimethylformamide (400 mL) was then added dropwise. The mixture was heated in an oil bath at 140° C. overnight. After cooling to room temperature, the mixture was quenched by addition of saturated aqueous ammonium chloride solution and concentrated under vacuum. The residual oil was taken up in water and extracted with diethyl ether. The organic extract was washed with water and brine, dried over magnesium sulfate and concentrated to an oil. Distillation under vacuum afforded the title compound (7.8 grams, 71%) as a clear oil.

B) 3-exo-Hydroxymethyl-8-oxabicyclo[3.2.1]octane-3-carboxylic acid ethyl ester

A 1.2M solution of diisobutylaluminum hydride in toluene (62.5 mL, 75 mmole) was added dropwise to a solution of 8-oxabicyclo[3.2.1]octane-3,3-dicarboxylic acid diethyl ester (7.8 grams, 30 mmole) in toluene (80 mL) at –40° C. The mixture was allowed to warm to 0° C. while stirring for a period of 3 hours. It was then cooled to –15° C. and ethanol (8 mL) was added slowly while maintaining this temperature. After stirring at –15° C. for 1 hour, sodium borohydride (1.1 grams, 30 mmole) was added. The mixture was stirred at room temperature overnight and was quenched by dropwise addition of saturated aqueous sodium sulfate solution. Ethyl acetate was added and, after stirring for 20 minutes, the insoluble material was removed by filtration through Celite™. The filtrate was washed with brine, dried over magnesium sulfate and concentrated to afford the title compound (5.1 grams, 80%) as a clear oil.

C) 3-exo-Hydroxymethyl-8-oxabicyclo[3.2.1]octane-3-carboxylic acid

Lithium hydroxide hydrate (2.5 grams, 59.5 mmole) was added to a solution of 3-exo-hydroxymethyl-8-oxabicyclo [3.2.1]octane-3-carboxylic acid ethyl ester (5.1 grams, 23.8 mmole) in a mixture of methanol (25 mL), tetrahydrofuran (25 mL) and water (2.5 mL). The mixture was heated at reflux overnight, cooled and quenched by addition of Amberlite IR-120™ ion exchange resin. After stirring for 20 minutes, the resin was removed by filtration, washing with tetrahydrofuran. Evaporation of the solvents and trituration of the residue with diethyl ether afforded the title compound (2.35 grams, 53%) as a white solid.

D) 3',8-Dioxaspiro[bicyclo[3.2.1]octane-3,1'-cyclobutane]-2'-one

Benzenesulfonylchloride (1.7 mL, 13.5 mmole) was added dropwise to a solution of 3-exo-hydroxymethyl-8-oxabicyclo[3.2.1]octane-3-carboxylic acid (2.3 grams, 12.3 mmole), triethylamine (3.4 mL, 24.7 mmole) and 4-dimethylaminopyridine (300 mg, 2.5 mmole) in methylene chloride (50 mL) at 0° C. The mixture was stirred at 0° C. for 1 hour, diluted with methylene chloride and washed with aqueous 1N hydrochloric acid solution, saturated aqueous sodium bicarbonate solution and brine. After drying over magnesium sulfate, the solvent was evaporated to provide the title compound as a white solid (1.8 grams, 90%).

E) 3-exo-[4-(4-Fluorophenoxy)phenylsulfanylmethyl]-8-oxabicyclo[3.2.1]octane-3-carboxylic acid A solution of 4-(4-fluorophenoxy)thiophenol (2.2 grams, 10 mmole) in tetrahydrofuran (10 mL) was added dropwise to a slurry of sodium hydride (270 mg, 11.3 mmole) in tetrahydrofuran (20 mL) at –10° C. The mixture was allowed to warm to room temperature while stirring for 30 minutes. After cooling again to –10° C., a solution of 3'8-dioxaspiro[bicyclo[3.2.1]octane-3,1'-cyclobutane]-2'-one (1.8 grams, 10 mmole) in tetrahydrofuran (20 mL) was added dropwise. The cooling bath was removed and stirring was continued at room temperature for 2 hours after which the mixture was quenched with aqueous 1N hydrochloric acid solution and extracted twice with methylene chloride. The combined organic extracts were washed with water and brine, dried over magnesium sulfate and concentrated to a solid. Recrystallization from diethyl ether/hexane afforded the title compound (1.8 grams (47%) as a white solid. Concentration of the mother liquor followed by chromatography on silica gel (2% methanol in chloroform as eluant) gave more of the the title compound (500 mg, 13%).

F) 3-exo[4-(4-Fluorophenoxy)phenylsulfanylmethyl]-8-oxabicyclo[3.2.1]octane-3-carboxylic acid benzyloxyamide To a solution of 3-exo-[4-(4-fluorophenoxy) benzenesulfanylmethyl]-8-oxabicyclo-[3.2.1]octane-3-carboxylic acid (1.0 grams, 2.6 mmole) and diisopropylethylamine (0.5 mL, 2.9 mmole) in N,N-dimethylformamide (20 mL) was added (benzotriazol-1-yloxy)tris-(dimethylamino)phoshonium hexafluoroborate (1.2 grams, 2.7 mmole). After stirring at room temperature for 2.5 hours, additional diisopropylethylamine (0.86 mL, 4.9 mmole) and O-benzylhydroxylamine hydrochloride (525 mg, 3.3 mmole) were added. The reaction mixture was stirred for 16 hours at 50° C. After concentration under vacuum, the residue was dissolved in ethyl acetate and washed sequentially with aqueous 1N hydrochloric acid solution, saturated aqueous sodium bicarbonate solution, and brine. The solution was dried over magnesium sulfate and concentrated to an oil from which the title compound, a white foam (405 mg, 32%) was isolated by chromatography (30% ethyl acetate in hexane as eluant).

G) 3-exo-[4-(4-Fluorophenoxy)phenylsulfonylmethyl]-8-oxabicyclo[3.2.1]octane-3-carboxylic acid benzyloxyamide Solid 57–85% meta-chloroperbenzoic acid (283 mg) was added to a solution of 3-exo-[4-(4-fluorophenoxy) phenylsulfanylmethyl]-8-oxabicyclo[3.2.1]octane-3-carboxylic acid benzyloxyamide in methylene chloride (15 mL). The resulting mixture was stirred at room temperature overnight, and was then quenched by addition of saturated aqueous sodium bisulfite solution. After dilution with methylene chloride, the organic layer was separated and washed with saturated aqueous sodium bicarbonate solution, water and brine. The organic layer was dried over magnesium sulfate and concentrated to give the title compound as a white foam (390 mg, 90%).

H) 3-exo-[4-(4-Fluorophenoxy)benzenesulfonylmethyl]-8-oxabicyclo-[3.2.1]-octane-3-carboxylic acid hydroxyamide A solution of 3-exo[4-(4-fluorophenoxy) benzenesulfonylmethyl]-8-oxabicyclo-[3.2.1]octane-3-carboxylic acid benzyloxyamide (390 mg, 0.74 mmole) in methanol (20 mL) was treated with 5% palladium on barium sulfate (195 mg) and hydrogenated at 3 atmospheres pressure for 3.5 hours in a Parr ™ shaker. The catalyst was removed by passage through a 0.45 μm nylon filter and the filtrate was concentrated to a white foam. Crystallization from a mixture of ethyl acetate and hexane provided the title compound as a white solid (230 mg, 71%).

M.p. 134°–139° C. $^1$H NMR ($d_6$-DMSO): δ 8.55 (br s, 1 H), 7.76 (d, J=7.5 Hz, 2 H), 7.30–7.26 (m, 2 H), 7.20–7.16 (m, 2 H), 7.09 (d, J=7.5 Hz, 2 H), 4.13 (br s, 2 H), 3.40 (s, 2 H), 2.24 (d, J=14.3 Hz, 2 H), 1.78–1.73 (m, 4 H), 1.57–1.55 (m, 2 H), MS m/e 434 (M—H). Further confirmation of structure and stereochemistry was carried out by single crystal X-ray crystallography.

EXAMPLE 3

3-(4-PHENOXYBENZENESULFONYLMETHYL)-8-OXABICYCLO[3.2.1]OCTANE-3-CARBOXYLIC ACID HYDROXYAMIDE

Prepared according to the same procedure as Example 2, using 4-phenoxyphenylthiophenol in step E.

$^1$H NMR ($d_6$-DMSO): δ 8.54 (br s, 1 H), 7.75 (d, J=8.9 Hz, 2 H), 7.44–7.40 (m, 2 H), 7.23 7.21 (m, 1 H), 7.11–7.07 (m, 4 H), 4.11 (br s, 2 H), 3.38 (s, 2 H), 2.22 (d, J=14.3 Hz, 2 H), 1.80–1.70 (m, 4 H), 1.60–1.50 (m, 2 H). MS m/e 416 (M—H).

EXAMPLE 4

3-EXO-(4'-FLUOROBIPHENYL-4-SULFONYLMETHYL)-8-OXABICYCLO[3.2.1]-OCTANE-3-CARBOXYLIC ACID HYDROXYAMIDE

Prepared according to the same procedure as Example 2 using 4'-fluorobiphenyl-4-thio in step E.

$^1$H NMR ($d_6$-DMSO): δ 10.60 (br s, 1 H), 8.58 (br s, 1 H), 7.88–7.85 (m, 4 H), 7.81–7.78 (m, 2 H), 7.36–7.31 (m, 2 H), 4.13 (br s, 2 H), 3.47 (s, 2 H), 2.25 (d, J=14.5 Hz, 2 H), 1.80–1.76 (m, 4 H), 1.60–1.55 (m, 2 H), MS m/e 418 (M—H).

EXAMPLE 5

3-EXO-[4-(4-CHLOROPHENOXY) BENZENESULFONYLMETHYL]-8-OXA-BICYCLO[3.2.1] OCTANE-3-CARBOXYLIC ACID HYDROXYAMIDE

A) 3-exo-[4-(4-Chlorophenoxy)phenylsulfanylmethyl]-8-oxabicyclo[3.2.1]-octane-3-carboxylic acid 4-(4-Chlorophenoxy)thiophenol (2.07 grams, 6.8 mmole) was added to a slurry of sodium hydride (180 mg, 7.5 mmole) in tetrahydrofuran (50 mL) room temperature. The mixture was allowed to stir at room temperature for 45 minutes. Solid 3',8-dioxaspiro[bicyclo[3.2.1]octane-3,1'-cyclobutane]-2'-one (1.04 grams, 6.2 mmole) was added and the reaction was stirred at room temperature overnight. The mixture was quenched with aqueous 1N hydrochloric acid solution and extracted twice with methylene chloride. The combined organic extracts were washed with brine, dried over magnesium sulfate and concentrated to a solid. Trituration with diethyl ether afforded, after filtration, the title compound as a white solid (1.47 grams, 59%).

B) 3-exo[4-(4-Chlorophenoxy)phenylsulfanylmethyl]-8-oxabicyclo[3.2.1]-octane-3-carboxylic acid hydroxyamide To a slurry of 3-exo-[4-(4-chlorophenoxy) phenylsulfanylmethyl]-8-oxabicyclo-[3.2.1]octane-3-carboxylic acid (1.47 grams, 3.63 mmole) in methylene chloride (20 mL) at room temperature was added dropwise oxalyl chloride (0.8 mL, 9.2 mmole) and N,N-dimethylformamide (1 drop). The mixture was stirred at room temperature overnight. After evaporation of volatiles under vacuum, the residue was dissolved in methylene chloride (20 mL), cooled to 0° C. and treated dropwise with O-trimethylsilylhydroxylamine (1.35 mL, 11.0 mmole). The resulting mixture was stirred at room temperature for 3.5 hours, cooled in an ice bath and quenched by addition of aqueous 1N hydrochloric acid solution, stirring at 0° C. for an additional 30 minutes. Following dilution with ethyl acetate, the organic layer was separated, washed with water and brine, dried over magnesium sulfate and concentrated to afford the title compound as a white foam (1.52 grams, 100%).

C) 3-exo-[4-(4-Chlorophenoxy)benzenesulfonylmethyl]-8-oxabicyclo[3.2.1] octane-3-carboxylic acid hydroxyamide Oxone™ (4.2 grams, 8.63 mmole) was added to a solution of 3-exo-[4-(4-chlorophenoxy)phenyl-sulfanylmethyl]-8-oxabicyclo[3.2.1]octane-3-carboxylic acid hydroxy-amide (1.52 grams, 3.63 mmole) in a mixture of water (30 mL), methanol (40 mL) and tetrahydrofuran (12 mL). The resulting mixture was stirred at room temperature overnight, diluted with water and extracted twice with ethyl acetate. The combined organic extracts were washed with brine, dried over magnesium sulfate and concentrated to a foam from which the title compound (846 mg, 52%) was isolated by chromatography on silica gel (4% methanol in chloroform as eluant).

$^1$H NMR ($d_6$-DMSO): δ 10.58 (br s, 1 H), 8.53 (br s, 1 H), 7.76 (d, J=8.6 Hz, 2 H), 7.46 (d, J=8.6 Hz, 2 H), 7.15–7.11 (m, 4 H), 4.11 (br s, 2 H), 3.40 (s, 2 H), 2.22 (d, J=14.3 Hz, 2 H), 1.76–1.71 (m, 4 H), 1.57–1.55 (m, 2 H), MS m/e 450 (M—H).

What is claimed is:

1. A compound of the formula

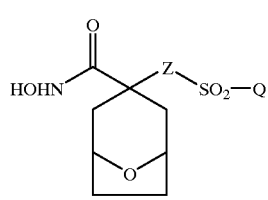

I wherein Z is >$CH_2$ or >$NR^1$;

R¹ is hydrogen, $(C_1-C_6)$alkyl, $(C_6-C_{10})$aryl$(C_1-C_6)$alkyl, $(C_2-C_9)$heteroaryl$(C_1-C_6)$alkyl or a group of the formula

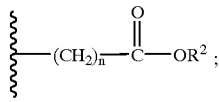

n is an integer from one to six;
R² is hydrogen or $(C_1-C_6)$alkyl;
Q is $(C_1-C_6)$alkyl, $(C_6-C_{10})$aryl, $(C_2-C_9)$heteroaryl, $(C_6-C_{10})$aryloxy$(C_1-C_6)$alkyl, $(C_6-C_{10})$aryloxy $(C_6-C_{10})$aryl, $(C_6-C_{10})$aryloxy$(C_2-C_9)$heteroaryl, $(C_6-C_{10})$aryl$(C_1-C_6)$alkyl, $(C_6-C_{10})$aryl$(C_6-C_{10})$aryl, $(C_6-C_{10})$aryl$(C_2-C_9)$heteroaryl, $(C_6-C_{10})$aryl$(C_6-C_{10})$aryl$(C_1-C_6)$alkyl, $(C_6-C_{10})$aryl$(C_6-C_{10})$aryl$(C_6-C_{10})$aryl, $(C_6-C_{10})$aryl$(C_6-C_{10})$aryl$(C_2-C_9)$heteroaryl, $C_2-C_9$)heteroaryl$(C_1-C_6)$alkyl, $(C_2-C_9)$heteroaryl $(C_6-C_{10})$aryl, $(C_2-C_9)$heteroaryl$(C_2-C_9)$heteroaryl, $(C_6-C_{10})$aryl$(C_1-C_6)$alkoxy$(C_1-C_6)$alkyl, $(C_6-C_{10})$aryl$(C_1-C_6)$alkoxy$(C_6-C_{10})$aryl, $(C_6-C_{10})$aryl$(C_1-C_6)$alkoxy$(C_2-C_9)$heteroaryl, $(C_2-C_9)$heteroaryloxy $(C_1-C_6)$alkyl, $(C_2-C_9)$heteroaryloxy$(C_6-C_{10})$aryl, $(C_2-C_9)$heteroaryloxy$(C_2-C_9)$heteroaryl, $(C_2-C_9)$ heteroaryl$(C_1-C_6)$alkoxy$(C_1-C_6)$alkyl, $(C_2-C_9)$ heteroaryl$(C_1-C_6)$alkoxy$(C_6-C_{10})$aryl, $(C_2-C_9)$ heteroaryl$(C_1-C_6)$alkoxy$(C_2-C_9)$heteroaryl, $(C_6-C_{10})$ aryloxy$((C_1-C_6)$alkyl$(C_6-C_{10})$aryl, $(C_6-C_{10})$aryloxy $(C_1-C_6)$alkyl$(C_2-C_9)$heteroaryl, $(C_2-C_9)$heteroaryloxy $(C_1-C_6)$alkyl$(C_6-C_{10})$aryl or $(C_2-C_9)$heteroaryloxy $(C_1-C_6)$alkyl$(C_2-C_9)$heteroaryl;

wherein each $(C_6-C_{10})$aryl or $(C_2-C_9)$heteroaryl moieties of said $(C_6-C_{10})$aryl, $(C_2-C_9)$heteroaryl, $(C_6-C_{10})$ aryloxy$(C_1-C_6)$alkyl, $(C_6-C_{10})$aryloxy$(C_6-C_{10})$aryl, $(C_6-C_{10})$aryloxy$(C_2-C_9)$heteroaryl, $(C_6-C_{10})$aryl $(C_1-C_6)$alkyl, $(C_6-C_{10})$aryl$(C_6-C_{10})$aryl, $(C_6-C_{10})$aryl $(C_2-C_9)$heteroaryl, $(C_6-C_{10})$aryl$(C_6-C_{10})$aryl$(C_1-C_6)$ alkyl, $(C_6-C_{10})$aryl$(C_6-C_{10})$aryl$(C_6-C_{10})$aryl, $(C_6-C_{10})$aryl$(C_6-C_{10})$aryl$(C_2-C_9)$heteroaryl, $(C_2-C_9)$ heteroaryl$(C_1-C_6)$alkyl, $(C_2-C_9)$heteroaryl$(C_6-C_{10})$ aryl, $(C_2-C_9)$heteroaryl$(C_2-C_9)$heteroaryl, $(C_6-C_{10})$ aryl$(C_1-C_6)$alkoxy$(C_1-C_6)$alkyl, $(C_6-C_{10})$aryl$(C_1-C_6)$ alkoxy$(C_6-C_{10})$aryl, $(C_6-C_{10})$aryl$(C_1-C_6)$alkoxy $(C_2-C_9)$heteroaryl, $(C_2-C_9)$heteroaryloxy$(C_1-C_6)$ alkyl, $(C_2-C_9)$heteroaryloxy$(C_6-C_{10})$aryl, $(C_2-C_9)$ heteroaryloxy$(C_2-C_9)$heteroaryl, $(C_2-C_9)$heteroaryl $(C_1-C_6)$alkoxy$(C_1-C_6)$alkyl, $(C_2-C_9)$heteroaryl $(C_1-C_6)$alkoxy$(C_6-C_{10})$aryl, $(C_2-C_9)$heteroaryl $(C_1-C_6)$alkoxy$(C_2-C_9)$heteroaryl, $(C_6-C_{10})$aryloxy $(C_1-C_6)$alkyl$(C_6-C_{10}$aryl, $(C_6-C_{10})$aryloxy$(C_1-C_6)$ alkyl$(C_2-C_9)$heteroaryl, $(C_2-C_9)$heteroaryloxy$(C_1-C_6)$ alkyl$(C_6-C_{10})$aryl or $(C_2-C_9)$heteroaryloxy$(C_1-C_6)$ alkyl$(C_2-C_9)$heteroaryl is optionally substituted on any of the ring carbon atoms capable of forming an additional bond by one or more substituents per ring independently selected from fluoro, chloro, bromo, $(C_1-C_6)$alkyl, $(C_1-C_6)$alkoxy, perfluoro$(C_1-C_3)$alkyl, perfluoro$(C_1-C_3)$alkoxy and $(C_6-C_{10})$aryloxy;

or a pharmaceutically acceptable salt thereof.

2. A compound according to claim 1, with stereochemistry as depicted by the formula

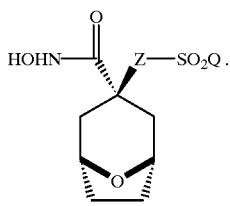

3. A compound according to claim 1, wherein Z is $CH_2$.
4. A compound according to claim 2, wherein Z is $CH_2$.
5. A compound according to claim 1, wherein Z is $>NR^1$ and R¹ is a group of the formula

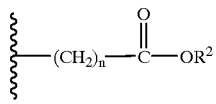

and wherein n is 2.

6. A compound according to claim 2, wherein Z is $>NR^1$ and R¹ is a group of the formula

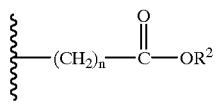

and wherein n is 2.

7. A compound according to claim 1, wherein Z is $>NR^1$ and R¹ is hydrogen.
8. A compound according to claim 2, wherein Z is $>NR^1$ and R¹ is hydrogen.
9. A compound according to claim 1, wherein Q is $(C_6-C_{10})$aryl, $(C_2-C_9)$heteroaryloxy$(C_6-C_{10})$aryl or $(C_6-C_{10})$aryloxy$(C_6-C_{10})$aryl, wherein each aryl or heteroaryl moiety of said $(C_6-C_{10})$aryl, $(C_2-C_9)$heteroaryloxy $(C_6-C_{10})$aryl or $(C_6-C_{10})$aryloxy$(C_6-C_{10})$aryl groups may be optionally substituted with one or more substituents independently selected from fluoro, chloro, bromo, $(C_1-C_6)$ alkyl, $((C_1-C_6)$alkoxy or perfluoro$(C_1-C_3)$alkyl.
10. A compound according to claim 2, wherein Q is $(C_6-C_{10})$aryl, $(C_2-C_9)$heteroaryloxy$(C_6-C_{10})$aryl or $(C_6-C_{10})$aryloxy$(C_6-C_{10})$aryl, wherein each aryl or heteroaryl moiety of said $(C_6-C_{10})$aryl, $(C_2-C_9)$heteroaryloxy $(C_6-C_{10})$aryl or $(C_6-C_{10})$aryloxy$(C_6-C_{10})$aryl groups may be optionally substituted with one or more substituents independently selected from fluoro, chloro, bromo, $(C_1-C_6)$ alkyl, $(C_1-C_6)$alkoxy or perfluoro$(C_1-C_3)$alkyl.
11. A compound according to claim 3, wherein Q is $(C_6-C_{10})$aryl, $(C_2-C_9)$heteroaryloxy$(C_6-C_{10})$aryl or $(C_6-C_{10})$aryloxy$(C_6-C_{10})$aryl, wherein each aryl or heteroaryl moiety of said $(C_6-C_{10})$aryl, $(C_2-C_9)$heteroaryloxy $(C_6-C_{10})$aryl or $(C_6-C_{10})$aryloxy$(C_6-C_{10})$aryl groups may be optionally substituted with one or more substituents independently selected from fluoro, chloro, bromo, $(C_1-C_6)$ alkyl, $(C_1-C_6)$alkoxy or perfluoro$(C_1-C_3)$alkyl.
12. A compound according to claim 5, wherein Q is $(C_6-C_{10})$aryl, $(C_2-C_9)$heteroaryloxy$(C_6-C_{10})$aryl or $(C_6-C_{10})$aryloxy$(C_6-C_{10})$aryl, wherein each aryl or heteroaryl moiety of said $(C_6-C_{10})$aryl, $(C_2-C_9)$heteroaryloxy $(C_6-C_{10})$aryl or $(C_6-C_{10})$aryloxy$(C_6-C_{10})$aryl groups may be optionally substituted with one or more substituents independently selected from fluoro, chloro, bromo, $(C_1-C_6)$ alkyl, $(C_1-C_6)$alkoxy or perfluoro$(C_1-C_3)$alkyl.

13. A compound according to claim 7, wherein Q is $(C_6-C_{10})$aryl, $(C_2-C_9)$heteroaryloxy$(C_6-C_{10})$aryl or $(C_6-C_{10})$aryloxy$(C_6-C_{10})$aryl, wherein each aryl or heteroaryl moiety of said $(C_6-C_{10})$aryl, $(C_2-C_9)$heteroaryloxy $(C_6-C_{10})$aryl or $(C_6-C_{10})$aryloxy$(C_6-C_{10})$aryl groups may be optionally substituted with one or more substituents independently selected from fluoro, chloro, bromo, $(C_1-C_6)$ alkyl, $(C_1-C_6)$alkoxy or perfluoro$(C_1-C_3)$alkyl.

14. A compound according to claim 8, wherein Q is $(C_6-C_{10})$aryl, $(C_2-C_9)$heteroaryloxy$(C_6-C_{10})$aryl or $(C_6-C_{10})$aryloxy$(C_6-C_{10})$aryl, wherein each aryl or heteroaryl moiety of said $(C_6-C_{10})$aryl, $(C_2-C_9)$heteroaryloxy $(C_6-C_{10})$aryl or $(C_6-C_{10})$aryloxy$(C_6-C_{10})$aryl groups may be optionally substituted with one or more substituents independently selected from fluoro, chloro, bromo, $(C_1-C_6)$ alkyl, $(C_1-C_6)$alkoxy or perfluoro$(C_1-C_3)$alkyl.

15. A compound according to claim 1, wherein Q is phenyl, pyridyloxyphenyl or phenoxyphenyl optionally substituted with one or more substituents independently selected from fluoro, chloro, bromo, $(C_1-C_6)$alkyl, $(C_1-C_6)$ alkoxy or perfluoro$(C_1-C_3)$alkyl.

16. A compound according to claim 2, wherein Q is phenyl, pyridyloxyphenyl or phenoxyphenyl optionally substituted with one or more substituents independently selected from fluoro, chloro, bromo, $(C_1-C_6)$alkyl, $(C_1-C_6)$ alkoxy or perfluoro$(C_1-C_3)$alkyl.

17. A compound according to claim 3, wherein Q is phenyl, pyridyloxyphenyl or phenoxyphenyl optionally substituted with one or more substituents independently selected from fluoro, chloro, bromo, $(C_1-C_6)$alkyl, $(C_1-C_6)$ alkoxy or perfluoro$(C_1-C_3)$alkyl.

18. A compound according to claim 5, wherein Q is phenyl, pyridyloxyphenyl or phenoxyphenyl optionally substituted with one or more substituents independently selected from fluoro, chloro, bromo, $(C_1-C_6)$alkyl, $(C_1-C_6)$ alkoxy or perfluoro$(C_1-C_3)$alkyl.

19. A compound according to claim 7, wherein Q is phenyl, pyridyloxyphenyl or phenoxyphenyl optionally substituted with one or more substituents independently selected from fluoro, chloro, bromo, $(C_1-C_6)$alkyl, $(C_1-C_6)$ alkoxy or perfluoro$(C_1-C_3)$alkyl.

20. A compound according to claim 8, wherein Q is phenyl, pyridyloxyphenyl or phenoxyphenyl optionally substituted with one or more substituents independently selected from fluoro, chloro, bromo, $(C_1-C_6)$alkyl, $(C_1-C_6)$ alkoxy or perfluoro$(C_1-C_3)$alkyl.

21. A compound according to claim 1, wherein said compound is selected from the groups consisting of 3-exo-[4-(4-fluorophenoxy)benzenesulfonylamino]-8-oxabicyclo[3.2.1]-octane-3-carboxylic acid hydroxyamide;

3-exo-[4-(4-fluorophenoxy)benzenesulfonylmethyl]-8-oxabicyclo-[3.2.1-octane-3-carboxylic acid hydroxyamide;

3-(4-phenoxybenzensulfonylmethyl)-8-oxabicyclo[3.2.1] octane-3-carboxylic acid hydroxyamide;

3-exo-(4-fluorobiphenyl-4-sulfonylmethyl]-8-oxabicyclo-[3.2.1]-octane-3-carboxylic acid hydroxyamide; and 3-exo-[4-(4-chlorophenoxy)benzenesulfonylmethyl]-8-oxabicyclo[3.2.1]octane-3-carboxylic acid hydroxyamide.

22. A pharmaceutical composition for the treatment of a condition selected from the group consisting of arthritis, inflammatory bowel disease, Crohn's disease, emphysema, chronic obstructive pulmonary disease, Alzheimer's disease, organ transplant toxicity, cachexia, allergic reactions, allergic contact hypersensitivity, cancer, tissue ulceration, restenosis, periodontal disease, epidemolysis bullosa, osteoporosis, loosening of artificial joint implants, atherosclerosis, aortic aneurysm, congestive heart failure, myocardial infarction, stroke, cerebral ischemia, head trauma, spinal cord injury, neuro-degenerative disorders, autoimmune disorders, Huntington's disease, Parkinson's disease, migraine, depression, peripheral neuropathy, pain, cerebral amyloid angiopathy, nootropic or cognition enhancement, amyotropic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis and septic shock in a mammal or a human, comprising an amount of a compound of claim 1 effective in such treatment and a pharmaceutically acceptable carrier.

23. A method for treating a condition selected from the group consisting of arthritis, inflammatory bowel disease, Crohn's disease, emphysema, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis, aortic aneursym, congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotropic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis and septic shock in a mammal or a human, comprising administering to said mammal an amount of a compound of claim 1, effective in treating such a condition.

24. A pharmaceutical composition for the treatment of a condition which can be treated by the inhibition of matrix metalloproteinases in a mammal or a human, comprising an amount of a compound of claim 1 effective in such treatment and a pharmaceutically acceptable carrier.

25. A pharmaceutical composition for the treatment of a condition which can be treated by the inhibition of a mammalian reprolysin in a mammal or a human, comprising an amount of a compound of claim 1 effective in such treatment and a pharmaceutically acceptable carrier.

26. A method for the inhibition of matrix metalloproteinases in a mammal or a human, comprising administering to said mammal an effective amount of a compound of claim 1.

27. A method for the inhibition of a mammalian reprolysin in a mammal or a human, comprising administering to said mammal an effective amount of a compound of claim 1.

* * * * *